United States Patent [19]

Frank

[11] Patent Number: 5,292,720

[45] Date of Patent: Mar. 8, 1994

[54] FORMATE ESTER INDANE COMPOUNDS

[75] Inventor: Walter C. Frank, Holland, Pa.

[73] Assignee: Union Camp Corporation, Princeton, N.J.

[21] Appl. No.: 79,008

[22] Filed: Jun. 18, 1993

[51] Int. Cl.$^5$ .............................................. A61K 7/46
[52] U.S. Cl. ...................................... 512/19; 560/139
[58] Field of Search .......................... 512/19; 560/139

[56] References Cited

FOREIGN PATENT DOCUMENTS 0301375 2/1989 European Pat. Off. .

OTHER PUBLICATIONS

Perrier, *Chem. Ber.*, vol. 33, p. 815 et seq. (1900).
Perrier, *Bull Soc. Chim. France*, p. 859 et seq. (1904).

*Primary Examiner*—James H. Reamer
*Attorney, Agent, or Firm*—Woodcock Washburn Kurtz Mackiewicz & Norris

[57] ABSTRACT

The present invention relates to novel formate ester indane compounds having fragrant musk-like aroma.

42 Claims, No Drawings

FORMATE ESTER INDANE COMPOUNDS

BACKGROUND OF THE INVENTION

The present invention relates to novel formate ester indane compounds having fragrant musk like aroma.

Musk has been a highly valued fragrance for decades, finding use in numerous products such as in perfumes, colognes, soaps, cosmetics, as well as others. Natural musk is obtained from the glands of the endangered tiny musk deer of Central Asia, *Moschus moschiferous*, commonly referred to as the Asian musk deer. Such natural musk, however, is extremely scarce and expensive. Accordingly, fragrance chemists around the world have spent considerable time and effort searching for synthetic products which duplicate or closely simulate the natural musk scent.

As a result of such research efforts, a number of different synthetic musks have been discovered. Among such synthetic compounds are the acetyl indanes described by Sprecker et al., U.S. Pat. No. 4,466,908, compounds of the formulas

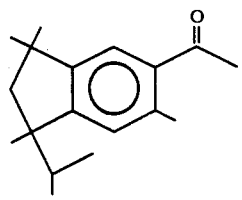

and

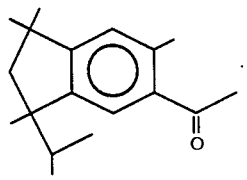

Similarly, Fehr et al., *Helvetica Chimica Acta*, Vol. 72, pp. 1537–1553 (1989) discusses such synthetic musks as those of the formula

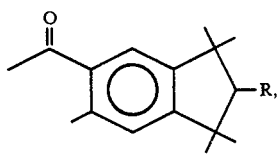

wherein R is either H or $CH_3$.

Traas et al., U.S. Pat. No. 4,352,748 discloses formylated and acetylated indane musks, including those of the formulas

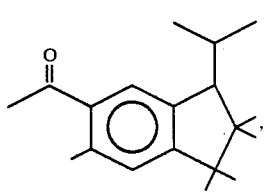

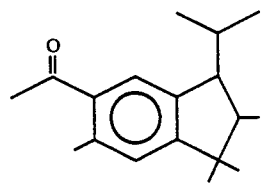

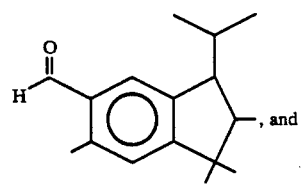

, and

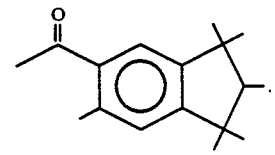

Other acetyl indanes, such as 6-acetyl-1,1,3,3,5-pentamethylindane, 5-acetyl-1,1,2,3,3 pentamethylindane and 6 acetyl-5 ethyl-1,1,2,3,3-pentamethylindane, are disclosed in French Patent No. 1,392,804 (as reported in Chemical Abstracts, Vol. 63, p. 1681d (1965)).

Cobb et al., U.S. Pat. No. 4,551,573, also discusses various indane compounds.

New and or better musk aroma compounds are needed to meet the demands of the fragrance industries. The present invention is directed to these, as well as other, important ends.

SUMMARY OF THE INVENTION

The present invention provides novel compounds of the formula [I]:

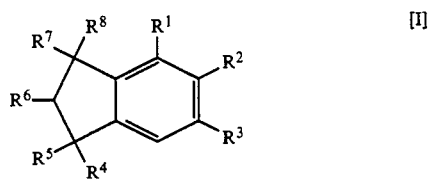

wherein
$R^1$ is H, $CH_3$, $CH_2CH_3$, $OCH_3$ or OH,
$R^2$ and $R^3$ are, independently, H, $CH_3$, $CH_2CH_3$, $OCH_3$, OH or OC(O)H,
$R^4$ and $R^7$ are, independently, H, $CH_3$, $CH_2CH_3$ or $CH(CH_3)_2$,
$R^5$ and $R^8$ are, independently H or $CH_3$, and
$R^6$ is H, $CH_3$ or $CH_2CH_3$,
provided that
(i) one of $R^2$ and $R^3$ is OC(O)H, and one of $R^2$ and $R^3$ is other than OC(O)H,
(ii) when $R^1$ is H, then $R^2$ and $R^3$ are other than $OCH_3$ or OH,
(iii) when $R^1$ is other than H, then $R^7$ is $CH_3$ or $CH_2CH_3$,
(iv) no more than one of $R^4$, $R^6$ or $R^7$ is $CH_2CH_3$ or $CH(CH_3)_2$,
(v) no more than one of $R^4$, $R^5$, $R^6$, $R^7$ and $R^8$ is H, (vi) when each of $R^1$, $R^3$, $R^4$ and $R^5$ are $CH_3$, then $R^8$ is H, (vii) when $R^4$ is $CH(CH_3)_2$, then at least one of $R^5$ or $R^6$ is H, (viii) when $R^7$ is $CH(CH_3)_2$, then at least one of $R^6$ or $R^8$ is H, (ix) when $R^1$ is $OCH_3$, then $R^2$ and $R^3$ are other than OH, and (x) when $R^1$ is OH, then $R^2$ and $R^3$ are other than OH or $OCH_3$.

The foregoing compounds possess an active musk aroma having utility in the fragrance industry. The compounds of the invention may be used alone, or in combination with carriers, additional perfumery materials, and/or other ingredients, to provide various products, such as perfumes, colognes, soaps, and cosmetics.

DETAILED DESCRIPTION OF THE INVENTION

As noted above, the present invention is directed to novel musk compounds of the formula [I]:

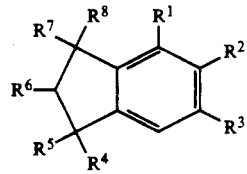

[I]

In the above formula [I], the R substituents may be selected as follows: $R^1$ may be selected from the group consisting of H, $CH_3$, $CH_2CH_3$, $OCH_3$ and OH; $R^2$ may be selected from the group consisting of H, $CH_3$, $CH_2CH_3$, $OCH_3$, OH and OC(O)H; $R^3$ may be selected from the group consisting of H, $CH_3$, $CH_2CH_3$, $OCH_3$, OH and OC(O)H; $R^4$ may be selected from the group consisting of H, $CH_3$, $CH_2CH_3$ and $CH(CH_3)_2$; $R^5$ may be selected from the group consisting of H and $CH_3$; $R^6$ may be selected from the group consisting of H, $CH_3$ and $CH_2CH_3$; $R^7$ may be selected from the group consisting of H, $CH_3$, $CH_2CH_3$ and $CH(CH_3)_2$; and $R^8$ may be selected from the group consisting of H and $CH_3$.

The foregoing selection of R substituents should, however, be made with the following qualifications in mind: that one of $R^2$ and $R^3$ is OC(O)H, and the other of $R^2$ and $R^1$ is other than OC(O)H; that when $R^1$ is H, then $R^2$ and $R^3$ are both other than $OCH_3$ or OH; that when $R^1$ is other than H, then $R^7$ is either $CH_3$ or $CH_2CH_3$; that no more than one of $R^4$, $R^6$ or $R^7$ is either $CH_2CH_3$ or $CH(CH_3)_2$; that no more than one of $R^4$, $R^5$, $R^6$, $R^7$ and $R^8$ is H; that when all of $R^1$, $R^3$, $R^4$ and $R^5$ are $CH_3$, then $R^8$ is H; that when $R^4$ is $CH(CH_3)_2$, then one or both of $R^5$ or $R^6$ is H; that when $R^7$ is $CH(CH_3)_2$, then one or both of $R^6$ or $R^8$ is H; that when $R^1$ is $OCH_3$, then $R^2$ and $R^3$ are both other than OH; and that when $R^1$ is OH, then $R^2$ and $R^3$ are both other than either OH or $OCH_3$.

For reasons of their fragrance characteristics, synthesis advantages, formulation benefits, and/or other values, the following are preferable classes of compounds within the scope of Formula [I]:

Compounds of Formula [I] wherein $R^2$ is OC(O)H.

Compounds of Formula [I] wherein at least one (that is, one or more) of $R^1$, $R^2$ and R are, independently, $OCH_3$ or OH.

Compounds of Formula [I] wherein at least one (that is, one or more) of $R^1$, $R^2$ and $R^3$ are $OCH_3$.

Compounds of Formula [I] wherein $R^1$ is H, $CH_3$, $CH_2CH_3$ or $OCH_3$, and $R^2$ and $R^3$ are, independently, H, $CH_3$, $CH_2CH_3$, $OCH_3$ or OC(O)H.

Compounds of Formula [I] wherein $R^1$ is H, $CH_3$ or $OCH_3$, and $R^2$ and $R^3$, independently, are H, $CH_3$, $OCH_3$ or OC(O)H.

Compounds of Formula [I] wherein at least one (that is, one or more) of $R^4$ or $R^7$ are H, $CH_3$ or $CH_2CH_3$.

Compounds of Formula [I] wherein $R^4$ and $R^7$ are, independently, $CH_3$, $CH_2CH_3$ or $CH(CH_3)_2$, and $R^5$ and $R^8$ are $CH_3$.

Compounds of Formula [I] wherein $R^4$ and $R^7$ are, independently, $CH_3$, $CH_2CH_3$ or $CH(CH_3)_2$, $R^5$ and $R^8$ are $CH_3$ and $R^6$ is $CH_3$ or $CH_2CH_3$.

Compounds of Formula [I] wherein $R^4$ is $CH(CH_3)_2$.

Specific compounds of Formula [I] which are most preferred, for reasons of fragrance characteristics, synthesis advantages, formulation benefits, and/or other values are as follows:

The compound of Formula [I] wherein compound of claim 1 wherein $R^1$ is $CH_3$, $R^2$ is OC(O)H, $R^3$ is $OCH_3$, $R^4$ is $CH_3$, $R^5$ is $CH_3$, $R^6$ is $CH_3$, $R^7$ is $CH_3$ and $R^8$ is $CH_3$.

The compound of Formula [I] wherein $R^1$ is $OCH_3$, $R^2$ is OC(O)H, $R^3$ is $CH_3$, $R^4$ is $CH_3$, $R^5$ is $CH_3$, $R^6$ is $CH_3$, $R^7$ is $CH_3$ and $R^8$ is $CH_3$.

The compound of Formula [I] wherein $R^1$ is $CH_3$, $R^2$ is OC(O)H, $R^3$ is $CH_3$, $R^4$ is $CH_2CH_3$, $R^5$ is $CH_3$, $R^6$ is H, $R^7$ is $CH_3$ and $R^8$ is $CH_3$.

The compound of Formula [I] wherein $R^1$ is $CH_3$, $R^2$ is OC(O)H, $R^3$ is $OCH_3$, $R^4$ is $CH_2CH_3$, $R^5$ is $CH_3$, $R^6$ is H, $R^7$ is $CH_3$ and $R^8$ is $CH_3$.

The compound of Formula [I] wherein $R^1$ is $CH_3$, $R^2$ is OC(O)H, $R^3$ is $OCH_3$, $R^4$ is $CH_3$, $R^5$ is $CH_3$, $R^6$ is H, $R^7$ is $CH_2CH_3$ and $R^8$ is $CH_3$.

The compound of Formula [I] wherein $R^1$ is $OCH_3$, $R^2$ is OC(O)H, $R^3$ is $CH_3$, $R^4$ is $CH_2CH_3$, $R^5$ is $CH_3$, $R^6$ is H, $R^7$ is $CH_3$ and $R^8$ is $CH_3$.

The compound of Formula [I] wherein $R^1$ is $OCH_3$, $R^2$ is OC(O)H, $R^3$ is $CH_3$, $R^4$ is $CH_3$, $R^5$ is $CH_3$, $R^6$ is H, $R^7$ is $CH_2CH_3$ and $R^8$ is $CH_3$.

The compound of Formula [I] wherein $R^1$ is H, $R^2$ is OC(O)H, $R^3$ is $CH_3$, $R^4$ is $CH_3$, $R^5$ is $CH_3$, $R^6$ is $CH_3$, $R^7$ is $CH_3$ and $R^8$ is $CH_3$.

The compound of Formula [I] wherein $R^1$ is H, $R^2$ is OC(O)H, $R^3$ is $CH_3$, $R^4$ is $CH_2CH_3$, $R^5$ is $CH_3$, $R^6$ is H, $R^7$ is $CH_3$ and $R^8$ is $CH_3$.

The compound of Formula [I] wherein $R^1$ is H, $R^2$ is OC(O)H, $R^3$ is $CH_3$, $R^4$ is $CH_3$, $R^5$ is $CH_3$, $R^6$ is H, $R^7$ is $CH_2CH_3$ and $R^8$ is $CH_3$.

The compound of Formula [I] wherein R is H, $R^2$ is OC(O)H, $R^3$ is $CH_3$, $R^4$ is $CH(CH_3)_2$, $R^5$ is $CH_3$, $R^6$ is H, $R^7$ is $CH_3$ and $R^8$ is $CH_3$.

The compound of Formula [I] wherein $R^1$ is H, $R^2$ is OC(O)H, $R^3$ is $CH_3$, $R^4$ is $CH_3$, $R^5$ is $CH_3$, $R^6$ is H, $R^7$ is $CH(CH_3)_2$ and $R^8$ is $CH_3$.

The compound of Formula [I] wherein $R^1$ is $CH_3$, $R^2$ is OC(O)H, $R^3$ is $CH_3$, $R^4$ is $CH(CH_3)_2$, $R^5$ is H, $R^6$ is $CH_3$, $R^7$ is $CH_3$ and $R^8$ is $CH_3$.

The compound of Formula [I] wherein $R^1$ is $CH_3$, $R^2$ is OC(O)H, $R^3$ is $OCH_3$, $R^4$ is $CH(CH_3)_2$, $R^5$ is H, $R^6$ is $CH_3$, $R^7$ is $CH_3$ and $R^8$ is $CH_3$.

The compound of Formula [I] wherein $R^1$ is $OCH_3$, $R^2$ is OC(O)H, $R^3$ is $CH_3$, $R^4$ is $CH(CH_3)_2$, $R^5$ is H, $R^6$ is $CH_3$, $R^7$ is $CH_3$ and $R^8$ is $CH_3$.

The compound of Formula [I] wherein $R^1$ is $OCH_3$, $R^2$ is $OC(O)H$, $R^3$ is $OCH_3$, $R^4$ is $CH(CH_3)_2$, $R^5$ is H, $R^6$ is $CH_3$, $R^7$ is $CH_3$ and $R^8$ is $CH_3$.

The compound of Formula [1] wherein $R^1$ is H, $R^2$ is $OC(O)H$, $R^3$ is $CH_3$, $R^4$ is $CH(CH_3)_2$, $R^5$ is H, $R^6$ is $CH_3$, $R^7$ is $CH_3$ and $R^8$ is $CH_3$.

The compound of Formula [I] wherein $R^1$ is H, $R^2$ is $OC(O)H$, $R^3$ is $CH_3$, $R^4$ is $CH_3$, $R^5$ is $CH_3$, $R^6$ is $CH_3$, $R^7$ is $CH(CH_3)$, and $R^8$ is H.

The novel formate ester indane compounds of the present invention may be prepared in various fashions. In the preferable protocol, alkylated indanes are first prepared, then formylated (that is, the radical —C(O)H is added to the benzene ring of the indane structure, to form an alkylated indane aldehyde), and then oxidized (that is, the radical —C(O)H on the benzene ring of the indane structure is oxidized to —OC(O)H, to form an alkylated indane ester), yielding the formate ester indane compounds of Formula [I]. Examples 1-11 below illustrate specific methodology which may be utilized for the preparation of compounds of the present invention.

In general, alkyl indane compounds or formylated alkyl indane compounds may be prepared by numerous synthetic routes which will be readily apparent to those skilled in the art, once armed with the present disclosure. Examples of suitable methodology include Fehr et al., U.S. Pat. No. 5,162,588, Cobb et al., U.S. Pat. No. 4,551,573, Gozenbach et al., U.S. Pat. No. 4,406,828, Traas et al., U.S. Pat. No. 4,352,748, Sprecker et al, U.S. Pat. Nos. 4,162,256 and 4,466,908, Wood et al., U.S. Pat. No. 3,509,215, Stofberg et al., U.S. Pat. No. 3,278,622, Frank, U.S. Pat. Nos. 5,095,152, 5,087,770, 5,087,785, and 5,206,217, Fehr et al., *Helvetica Chimica Acta*, Vol. 72, pp. 1537-1553 (1989), European Patent Application Publication No. 0 393 742, Japanese Patent No. SHO 50-40761, and French Patent No. 1 392 804 (also reported in Chemical Abstracts, Vol. 63, p. 1681d (1965), the disclosures of each of which are hereby incorporated herein by reference, in their entirety.

In accordance with Frank, U.S. Pat. No. 5,087,785, for example, secondary alkyl indanes may be prepared by isomerizing an alkylated tetrahydronaphthalene in the presence of (i) a Lewis acid (the Lewis acid being present in an amount of less than about 50 mole percent based on the amount of the alkylated tetrahydronaphthalene), and (ii) a solvent which can be a halogenated or unhalogenated solvent and, optionally, (iii) a phase transfer agent. Exemplary Lewis acids include titanium chloride, aluminum chloride and aluminum bromide. Exemplary halogenated solvents include dichloromethane, trichloromethane and 1,2-dichloroethane, and exemplary unhalogenated solvents include cyclohexane. Exemplary phase transfer agents include methyltrioctylammonium chloride and a mixture of methyltrioctylammonium chloride and methyltridecylammonium chloride (marketed under the trademark ADOGEN-464 ™, by Sherex Co., Dublin, Ohio).

In the foregoing process, the molar proportions of the reagents can be varied over a relatively wide range, provided that the Lewis acid is present in an amount of less than about 50 mole percent based on the amount of the alkylated tetrahydronaphthalene starting material, the precise amounts of the reagents being dependent upon such factors as the particular solvent employed, the presence or absence of a phase transfer agent, and the specific tetrahydronaphthalene starting material and other reaction conditions such as time, temperature, pressure, etc. Suitable reagent amounts will be well within the ambit of those skilled in the art, once armed with the present disclosures.

Although, in general, the molar proportions of the reagents employed in the process may be relatively widely varied, for best results, however, it is important to maintain a ratio of less than one mole of phase transfer agent per mole of Lewis acid. Preferably, the molar ratio is about 0.8 to 1.0, more preferably about 0.5 to 1.0, phase transfer agent to Lewis acid.

The subject isomerization reaction may be carried out in any suitable vessel which provides sufficient contacting between the Lewis acid, the phase transfer agent and the other reactants. For simplicity, a stirred batch reactor can be employed. The reaction vessel used should be resistant to the possible corrosive nature of the Lewis acid, such as a glass lined vessel. The reagents of the present process may be added to the vessel in any order, although generally the solvent, the alkylated tetrahydronaphthalene, and any phase transfer agent are added first, followed by Lewis acid addition. The reaction may be carried out over a wide temperature range, but is preferably carried out at temperatures from about 0° C. to about 20° C. The pressure at which the reaction is carried out and the type of atmosphere are not critical. Generally, the isomerization reaction proceeds to equilibrium in about 1 to about 8 hours.

Product can be recovered from the reaction mixture by first quenching the reaction mixture in cold water or on crushed ice, preferably on ice, and then processing the mixture in the usual manner for Friedel—Crafts reactions to extract the indane compounds. Suitable extraction protocol is described, for example, in George A. Olah, *Friedel-Crafts And Related Reactions*, Vols. 1 and 2 (Interscience Publishers, John Wiley and Sons, New York, N.Y. 1964), the disclosures of which are hereby incorporated by reference in their entirety. Typically, following quenching and the resultant phase separation, the organic layer is washed an additional time with water to aid in removal of the Lewis acid. One or more additional washings can be carried out with dilute alkali solution to further aid Lewis acid removal. The resultant product is generally a mixture of the alkylated tetrahydronaphthalene starting material and the desired secondary alkyl indane isomerates. A more purified product may be obtained by subjecting the washed reaction mixture to reduced pressure fractional distillation, commercial chromatographic separation or other separation means known to those skilled in the art.

Alkylated tetrahydronaphthalene starting materials may be obtained commercially, or prepared using numerous well known procedures including those disclosed in Frank, U.S. Pat. Nos. 4,877,911, 4,877,914, 4,877,910, 4,877,916, 4,877,915, 4,877,913 and 4,877,912, Cobb et al., U.S. Pat. No. 4,551,573, Japanese Patent No. SHO 57-40420, Wood, U.S. Pat. No. 3,246,044, Wood et al., U.S. Pat. No. 3,856,875, Sato et al., U.S. Pat. No. 4,284,818, Kahn, U.S. Pat. No. 3,379,785, Suzukamo et al., U.S. Pat. No. 4,767,882, the disclosures of each of which are hereby incorporated herein by reference, in their entirety.

Alkyl indane compounds may then be formylated using conventional formylation technology. Specifically, to prepare formylated indane compounds, the alkyl indanes are preferably reacted with α,α-dichloromethyl methyl ether, in a solvent such as an organic solvent (preferably a halogenated organic solvent such as, for example, anhydrous dichloromethane), in the presence of a Lewis acid (preferably titanium chloride; $TiCl_4$). Other suitable halogenated solvents and Lewis acids are discussed above, and will be readily apparent to those skilled in the art, once armed with the present disclosures. In general, formylation methods are well known in the art and are described, for example, in *Organic Synthesis*, Collective Vol. 5, pp. 49–50 (John Wiley & Sons, 1973), the disclosures of which are incorporated herein by reference, in their entirety.

To prepare the formate ester indane compounds of Formula [I], the formylated indanes may then be oxidized, using conventional oxidation technology, producing compounds having a very fine, musk-like fragrance, a characteristic which renders them highly valuable for use in the perfumery industry. Specifically, to produce the formate ester compounds of the invention, a Baeyer-Villager-type reaction is preferably employed. In accordance with that process, the formylated compounds may be reacted with a peracid, preferably meta-chloroperbenzoic acid, in a solvent such as an organic solvent, preferably a halogenated organic solvent such as, for example, anhydrous methylene chloride. Other suitable peracids include perfluroacetic and peracetic acids. Other suitable halogenated solvents are as discussed previously. Such oxidation methods are described, for example, in Carey, Francis A., and Richard J. Sundberg, *Advanced Organic Chemistry*, Part B, pp. 383–386 (Plenum Press, New York 1977), Harrison, Ian T. and Harrison, Shuyen, *Compendium of Organic Synthetic Methods*, p. 84, John Wiley & Sons, New York, N.Y. (1971), March, Jerry, *Advanced Organic Chemistry*, 4th ed., John Wiley & Sons, New York, N.Y. (1992), Godfrey et al., J.C.S. Perkin I, pp. 1353–1354 (1974), Hannan et al., *J. Org. Chem.*, Vol. 44, No. 13, pp. 2153–2158 (1979), Nakaido et al., *J. Org. Chem.*, Vol. 49, pp. 4740–4741 (1984), Syper, *Synthesis*, pp. 167–172 (March 1989), Huang et al., *J. Chem. Research (Synop)*, pp. 292–293 (1991), the disclosures of each of which are hereby incorporated herein by reference, in their entirety.

Further purification of the formate ester indane compounds of Formula [I] may be carried out, if desired, using, for example, standard fractional distillation techniques, as well as other conventional extraction, distillation, crystallization and chromatography techniques, and the like.

Exemplary novel formate ester indane compounds within the scope of Formula [I] are shown in Table I below.

TABLE I

| Compound | $R^1$ | $R^2$ | $R^3$ | $R^4$ | $R^5$ | $R^6$ | $R^7$ | $R^8$ |
|---|---|---|---|---|---|---|---|---|
| 1 | H | H | OC(O)H | H | $CH_3$ | $CH_3$ | $CH_3$ | $CH_3$ |
| 2 | H | H | OC(O)H | H | $CH_3$ | $CH_3$ | $CH_2CH_3$ | $CH_3$ |
| 3 | H | H | OC(O)H | H | $CH_3$ | $CH_2CH_3$ | $CH_3$ | $CH_3$ |
| 4 | H | H | OC(O)H | $CH_3$ | $CH_3$ | H | $CH_3$ | $CH_3$ |
| 5 | H | H | OC(O)H | $CH_3$ | $CH_3$ | H | $CH_2CH_3$ | $CH_3$ |
| 6 | H | H | OC(O)H | $CH_3$ | $CH_3$ | H | $CH(CH_3)_2$ | $CH_3$ |
| 7 | H | H | OC(O)H | $CH_3$ | $CH_3$ | $CH_3$ | H | $CH_3$ |
| 8 | H | H | OC(O)H | $CH_3$ | $CH_3$ | $CH_2CH_3$ | H | $CH_3$ |
| 9 | H | H | OC(O)H | $CH_3$ | $CH_3$ | $CH_3$ | $CH_2CH_3$ | H |
| 10 | H | H | OC(O)H | $CH_3$ | $CH_3$ | $CH_3$ | $CH_2CH_3$ | H |
| 11 | H | H | OC(O)H | $CH_3$ | $CH_3$ | $CH_2CH_3$ | $CH_3$ | H |
| 12 | H | H | OC(O)H | $CH_2CH_3$ | H | $CH_3$ | $CH_3$ | $CH_3$ |
| 13 | H | H | OC(O)H | $CH_2CH_3$ | $CH_3$ | H | $CH_3$ | $CH_3$ |
| 14 | H | H | OC(O)H | $CH_2CH_3$ | $CH_3$ | $CH_3$ | H | $CH_3$ |
| 15 | H | H | OC(O)H | $CH(CH_3)_2$ | H | $CH_3$ | $CH_3$ | $CH_3$ |
| 16 | H | H | OC(O)H | $CH(CH_3)_2$ | $CH_3$ | H | $CH_3$ | $CH_3$ |
| 17 | H | $CH_3$ | OC(O)H | H | $CH_3$ | $CH_3$ | $CH_3$ | $CH_3$ |
| 18 | H | $CH_3$ | OC(O)H | H | $CH_3$ | $CH_3$ | $CH_2CH_3$ | $CH_3$ |
| 19 | H | $CH_3$ | OC(O)H | H | $CH_3$ | $CH_2CH_3$ | $CH_3$ | $CH_3$ |
| 20 | H | $CH_3$ | OC(O)H | $CH_3$ | $CH_3$ | H | $CH_3$ | $CH_3$ |
| 21 | H | $CH_3$ | OC(O)H | $CH_3$ | $CH_3$ | H | $CH_2CH_3$ | $CH_3$ |
| 22 | H | $CH_3$ | OC(O)H | $CH_3$ | $CH_3$ | H | $CH(CH_3)_2$ | $CH_2$ |
| 23 | H | $CH_3$ | OC(O)H | $CH_3$ | $CH_3$ | $CH_3$ | H | $CH_3$ |
| 24 | H | $CH_3$ | OC(O)H | $CH_3$ | $CH_3$ | $CH_2CH_3$ | H | $CH_3$ |
| 25 | H | $CH_3$ | OC(O)H | $CH_3$ | $CH_3$ | $CH_3$ | $CH_2CH_3$ | H |
| 26 | H | $CH_3$ | OC(O)H | $CH_3$ | $CH_3$ | $CH_3$ | $CH(CH_3)_2$ | H |
| 27 | H | $CH_3$ | OC(O)H | $CH_2CH_3$ | H | $CH_3$ | $CH_3$ | $CH_3$ |
| 28 | H | $CH_3$ | OC(O)H | $CH_2CH_3$ | $CH_3$ | H | $CH_3$ | $CH_3$ |
| 29 | H | $CH_3$ | OC(O)H | $CH_2CH_3$ | $CH_3$ | $CH_3$ | H | $CH_3$ |
| 30 | H | $CH_3$ | OC(O)H | $CH(CH_3)_2$ | H | $CH_3$ | $CH_3$ | $CH_3$ |
| 31 | H | $CH_3$ | OC(O)H | $CH(CH_3)_2$ | $CH_3$ | H | $CH_3$ | $CH_3$ |
| 32 | H | $CH_2CH_3$ | OC(O)H | H | $CH_3$ | $CH_3$ | $CH_3$ | $CH_3$ |
| 33 | H | $CH_2CH_3$ | OC(O)H | H | $CH_3$ | $CH_3$ | $CH_2CH_3$ | $CH_3$ |
| 34 | H | $CH_2CH_3$ | OC(O)H | H | $CH_3$ | $CH_2CH_3$ | $CH_3$ | $CH_3$ |
| 35 | H | $CH_2CH_3$ | OC(O)H | $CH_3$ | $CH_3$ | H | $CH_3$ | $CH_3$ |
| 36 | H | $CH_2CH_3$ | OC(O)H | $CH_3$ | $CH_3$ | H | $CH_2CH_3$ | $CH_3$ |
| 37 | H | $CH_2CH_3$ | OC(O)H | $CH_3$ | $CH_3$ | H | $CH(CH_3)_2$ | $CH_3$ |
| 38 | H | $CH_2CH_3$ | OC(O)H | $CH_3$ | $CH_3$ | $CH_3$ | H | $CH_3$ |
| 39 | H | $CH_2CH_3$ | OC(O)H | $CH_3$ | $CH_3$ | $CH_2CH_3$ | H | $CH_3$ |
| 40 | H | $CH_2CH_3$ | OC(O)H | $CH_3$ | $CH_3$ | $CH_3$ | $CH_2CH_3$ | H |
| 41 | H | $CH_2CH_3$ | OC(O)H | $CH_3$ | $CH_3$ | $CH_3$ | $CH(CH_3)_2$ | H |
| 42 | H | $CH_2CH_3$ | OC(O)H | $CH_2CH_3$ | H | $CH_3$ | $CH_3$ | $CH_3$ |
| 43 | H | $CH_2CH_3$ | OC(O)H | $CH_2CH_3$ | $CH_3$ | H | $CH_3$ | $CH_3$ |
| 44 | H | $CH_2CH_3$ | OC(O)H | $CH_2CH_3$ | $CH_3$ | $CH_3$ | H | $CH_3$ |
| 45 | H | $CH_2CH_3$ | OC(O)H | $CH(CH_3)_2$ | H | $CH_3$ | $CH_3$ | $CH_3$ |
| 46 | H | $CH_2CH_3$ | OC(O)H | $CH(CH_3)_2$ | $CH_3$ | H | $CH_3$ | $CH_3$ |
| 47 | $CH_3$ | H | OC(O)H | H | $CH_3$ | $CH_3$ | $CH_3$ | $CH_3$ |
| 48 | $CH_3$ | H | OC(O)H | H | $CH_3$ | $CH_3$ | $CH_2CH_3$ | $CH_3$ |
| 49 | $CH_3$ | H | OC(O)H | H | $CH_3$ | $CH_2CH_3$ | $CH_3$ | $CH_3$ |

TABLE I-continued

| Compound | R¹ | R² | R³ | R⁴ | R⁵ | R⁶ | R⁷ | R⁸ |
|---|---|---|---|---|---|---|---|---|
| 50 | CH₃ | H | OC(O)H | CH₃ | CH₃ | H | CH₃ | CH₃ |
| 51 | CH₃ | H | OC(O)H | CH₃ | CH₃ | H | CH₂CH₃ | CH₃ |
| 52 | CH₃ | H | OC(O)H | CH₃ | CH₃ | CH₃ | CH₃ | H |
| 53 | CH₃ | H | OC(O)H | CH₃ | CH₃ | CH₃ | CH₂CH₃ | H |
| 54 | CH₃ | H | OC(O)H | CH₃ | CH₃ | CH₂CH₃ | CH₃ | H |
| 55 | CH₃ | H | OC(O)H | CH₂CH₃ | H | CH₃ | CH₃ | CH₃ |
| 56 | CH₃ | H | OC(O)H | CH₂CH₃ | CH₃ | H | CH₃ | CH₃ |
| 57 | CH₃ | H | OC(O)H | CH₂CH₃ | CH₃ | CH₃ | CH₃ | H |
| 58 | CH₃ | H | OC(O)H | CH(CH₃)₂ | H | CH₃ | CH₃ | CH₃ |
| 59 | CH₃ | H | OC(O)H | CH(CH₃)₂ | CH₃ | H | CH₃ | CH₃ |
| 60 | CH₃ | CH₃ | OC(O)H | H | CH₃ | CH₃ | CH₃ | CH₃ |
| 61 | CH₃ | CH₃ | OC(O)H | H | CH₃ | CH₃ | CH₂CH₃ | CH₃ |
| 62 | CH₃ | CH₃ | OC(O)H | H | CH₃ | CH₂CH₃ | CH₃ | CH₃ |
| 63 | CH₃ | CH₃ | OC(O)H | CH₃ | CH₃ | H | CH₃ | CH₃ |
| 64 | CH₃ | CH₃ | OC(O)H | CH₃ | CH₃ | H | CH₂CH₃ | CH₃ |
| 65 | CH₃ | CH₃ | OC(O)H | CH₃ | CH₃ | CH₃ | CH₃ | H |
| 66 | CH₃ | CH₃ | OC(O)H | CH₃ | CH₃ | CH₃ | CH₂CH₃ | H |
| 67 | CH₃ | CH₃ | OC(O)H | CH₃ | CH₃ | CH₂CH₃ | CH₃ | H |
| 68 | CH₃ | CH₃ | OC(O)H | CH₂CH₃ | H | CH₃ | CH₃ | CH₃ |
| 69 | CH₃ | CH₃ | OC(O)H | CH₂CH₃ | CH₃ | H | CH₃ | CH₃ |
| 70 | CH₃ | CH₃ | OC(O)H | CH₂CH₃ | CH₃ | CH₃ | CH₃ | H |
| 71 | CH₃ | CH₃ | OC(O)H | CH(CH₃)₂ | H | CH₃ | CH₃ | CH₃ |
| 72 | CH₃ | CH₃ | OC(O)H | CH(CH₃)₂ | CH₃ | H | CH₃ | CH₃ |
| 73 | CH₃ | CH₂CH₃ | OC(O)H | H | CH₃ | CH₃ | CH₃ | CH₃ |
| 74 | CH₃ | CH₂CH₃ | OC(O)H | H | CH₃ | CH₃ | CH₂CH₃ | CH₃ |
| 75 | CH₃ | CH₂CH₃ | OC(O)H | H | CH₃ | CH₂CH₃ | CH₃ | CH₃ |
| 76 | CH₃ | CH₂CH₃ | OC(O)H | CH₃ | CH₃ | H | CH₃ | CH₃ |
| 77 | CH₃ | CH₂CH₃ | OC(O)H | CH₃ | CH₃ | H | CH₂CH₃ | CH₃ |
| 78 | CH₃ | CH₂CH₃ | OC(O)H | CH₃ | CH₃ | CH₃ | CH₃ | H |
| 79 | CH₃ | CH₂CH₃ | OC(O)H | CH₃ | CH₃ | CH₃ | CH₂CH₃ | H |
| 80 | CH₃ | CH₂CH₃ | OC(O)H | CH₃ | CH₃ | CH₂CH₃ | CH₃ | H |
| 81 | CH₃ | CH₂CH₃ | OC(O)H | CH₂CH₃ | H | CH₃ | CH₃ | CH₃ |
| 82 | CH₃ | CH₂CH₃ | OC(O)H | CH₂CH₃ | CH₃ | H | CH₃ | CH₃ |
| 83 | CH₃ | CH₂CH₃ | OC(O)H | CH₂CH₃ | CH₃ | CH₃ | CH₃ | H |
| 84 | CH₃ | CH₂CH₃ | OC(O)H | CH(CH₃)₂ | H | CH₃ | CH₃ | CH₃ |
| 85 | CH₃ | CH₂CH₃ | OC(O)H | CH(CH₃)₂ | CH₃ | H | CH₃ | CH₃ |
| 86 | CH₃ | OC(O)H | H | H | CH₃ | CH₃ | CH₃ | CH₃ |
| 87 | CH₃ | OC(O)H | H | H | CH₃ | CH₃ | CH₂CH₃ | CH₃ |
| 88 | CH₃ | OC(O)H | H | H | CH₃ | CH₂CH₃ | CH₃ | CH₃ |
| 89 | CH₃ | OC(O)H | H | CH₃ | CH₃ | H | CH₃ | CH₃ |
| 90 | CH₃ | OC(O)H | H | CH₃ | CH₃ | H | CH₂CH₃ | CH₃ |
| 91 | CH₃ | OC(O)H | H | CH₃ | CH₃ | CH₃ | CH₃ | H |
| 92 | CH₃ | OC(O)H | H | CH₃ | CH₃ | CH₃ | CH₂CH₃ | H |
| 93 | CH₃ | OC(O)H | H | CH₃ | CH₃ | CH₂CH₃ | CH₃ | H |
| 94 | CH₃ | OC(O)H | H | CH₂CH₃ | H | CH₃ | CH₃ | CH₃ |
| 95 | CH₃ | OC(O)H | H | CH₂CH₃ | CH₃ | H | CH₃ | CH₃ |
| 96 | CH₃ | OC(O)H | H | CH₂CH₃ | CH₃ | CH₃ | CH₃ | H |
| 97 | CH₃ | OC(O)H | H | CH(CH₃)₂ | H | CH₃ | CH₃ | CH₃ |
| 98 | CH₃ | OC(O)H | H | CH(CH₃)₂ | CH₃ | H | CH₃ | CH₃ |
| 99 | CH₃ | OC(O)H | CH₃ | H | CH₃ | CH₃ | CH₃ | CH₃ |
| 100 | CH₃ | OC(O)H | CH₃ | H | CH₃ | CH₃ | CH₂CH₃ | CH₃ |
| 101 | CH₃ | OC(O)H | CH₃ | H | CH₃ | CH₂CH₃ | CH₃ | CH₃ |
| 102 | CH₃ | OC(O)H | CH₃ | CH₃ | CH₃ | CH₃ | CH₃ | H |
| 103 | CH₃ | OC(O)H | CH₃ | CH₃ | CH₃ | CH₃ | CH₂CH₃ | H |
| 104 | CH₃ | OC(O)H | CH₃ | CH₃ | CH₃ | CH₂CH₃ | CH₃ | H |
| 105 | CH₃ | OC(O)H | CH₃ | CH₂CH₃ | H | CH₃ | CH₃ | CH₃ |
| 106 | CH₃ | OC(O)H | CH₃ | CH₂CH₃ | CH₃ | H | CH₃ | CH₃ |
| 107 | CH₃ | OC(O)H | CH₃ | CH₂CH₃ | CH₃ | CH₃ | CH₃ | H |
| 108 | CH₃ | OC(O)H | CH₃ | CH(CH₃)₂ | H | CH₃ | CH₃ | CH₃ |
| 109 | CH₃ | OC(O)H | CH₃ | CH(CH₃)₂ | CH₃ | H | CH₃ | CH₃ |
| 110 | CH₃ | OC(O)H | CH₂CH₃ | H | CH₃ | CH₃ | CH₃ | CH₃ |
| 111 | CH₃ | OC(O)H | CH₂CH₃ | H | CH₃ | CH₃ | CH₂CH₃ | CH₃ |
| 112 | CH₃ | OC(O)H | CH₂CH₃ | H | CH₃ | CH₂CH₃ | CH₃ | CH₃ |
| 113 | CH₃ | OC(O)H | CH₂CH₃ | CH₃ | CH₃ | H | CH₃ | CH₃ |
| 114 | CH₃ | OC(O)H | CH₂CH₃ | CH₃ | CH₃ | H | CH₂CH₃ | CH₃ |
| 115 | CH₃ | OC(O)H | CH₂CH₃ | CH₃ | CH₃ | CH₃ | CH₃ | H |
| 116 | CH₃ | OC(O)H | CH₂CH₃ | CH₃ | CH₃ | CH₃ | CH₂CH₃ | H |
| 117 | CH₃ | OC(O)H | CH₂CH₃ | CH₃ | CH₃ | CH₂CH₃ | CH₃ | H |
| 118 | CH₃ | OC(O)H | CH₂CH₃ | CH₂CH₃ | H | CH₃ | CH₃ | CH₃ |
| 119 | CH₃ | OC(O)H | CH₂CH₃ | CH₂CH₃ | CH₃ | H | CH₃ | CH₃ |
| 120 | CH₃ | OC(O)H | CH₂CH₃ | CH₂CH₃ | CH₃ | CH₃ | CH₃ | H |
| 121 | CH₃ | OC(O)H | CH₂CH₃ | CH(CH₃)₂ | H | CH₃ | CH₃ | CH₃ |
| 122 | CH₃ | OC(O)H | CH₂CH₃ | CH(CH₃)₂ | CH₃ | H | CH₃ | CH₃ |
| 123 | CH₂CH₃ | H | OC(O)H | H | CH₃ | CH₃ | CH₃ | CH₃ |
| 124 | CH₂CH₃ | H | OC(O)H | H | CH₃ | CH₃ | CH₂CH₃ | CH₃ |
| 125 | CH₂CH₃ | H | OC(O)H | H | CH₃ | CH₂CH₃ | CH₃ | CH₃ |
| 126 | CH₂CH₃ | H | OC(O)H | CH₃ | CH₃ | H | CH₃ | CH₃ |
| 127 | CH₂CH₃ | H | OC(O)H | CH₃ | CH₃ | H | CH₂CH₃ | CH₃ |
| 128 | CH₂CH₃ | H | OC(O)H | CH₃ | CH₃ | CH₃ | CH₃ | H |
| 129 | CH₂CH₃ | H | OC(O)H | CH₃ | CH₃ | CH₃ | CH₂CH₃ | H |
| 130 | CH₂CH₃ | H | OC(O)H | CH₃ | CH₃ | CH₂CH₃ | CH₃ | H |

TABLE I-continued

| Compound | R¹ | R² | R³ | R⁴ | R⁵ | R⁶ | R⁷ | R⁸ |
|---|---|---|---|---|---|---|---|---|
| 131 | CH₂CH₃ | H | OC(O)H | CH₂CH₃ | H | CH₃ | CH₃ | CH₃ |
| 132 | CH₂CH₃ | H | OC(O)H | CH₂CH₃ | CH₃ | H | CH₃ | CH₃ |
| 133 | CH₂CH₃ | H | OC(O)H | CH₂CH₃ | CH₃ | CH₃ | CH₃ | H |
| 134 | CH₂CH₃ | H | OC(O)H | CH(CH₃)₂ | H | CH₃ | CH₃ | CH₃ |
| 135 | CH₂CH₃ | H | OC(O)H | CH(CH₃)₂ | CH₃ | H | CH₃ | CH₃ |
| 136 | CH₂CH₃ | CH₃ | OC(O)H | H | CH₃ | CH₃ | CH₃ | CH₃ |
| 137 | CH₂CH₃ | CH₃ | OC(O)H | H | CH₃ | CH₃ | CH₂CH₃ | CH₃ |
| 138 | CH₂CH₃ | CH₃ | OC(O)H | H | CH₃ | CH₂CH₃ | CH₃ | CH₃ |
| 139 | CH₂CH₃ | CH₃ | OC(O)H | CH₃ | CH₃ | H | CH₃ | CH₃ |
| 140 | CH₂CH₃ | CH₃ | OC(O)H | CH₃ | CH₃ | H | CH₂CH₃ | CH₃ |
| 141 | CH₂CH₃ | CH₃ | OC(O)H | CH₃ | CH₃ | CH₃ | CH₃ | H |
| 142 | CH₂CH₃ | CH₃ | OC(O)H | CH₃ | CH₃ | CH₃ | CH₂CH₃ | H |
| 143 | CH₂CH₃ | CH₃ | OC(O)H | CH₃ | CH₃ | CH₂CH₃ | CH₃ | H |
| 144 | CH₂CH₃ | CH₃ | OC(O)H | CH₂CH₃ | H | CH₃ | CH₃ | CH₃ |
| 145 | CH₂CH₃ | CH₃ | OC(O)H | CH₂CH₃ | CH₃ | H | CH₃ | CH₃ |
| 146 | CH₂CH₃ | CH₃ | OC(O)H | CH₂CH₃ | CH₃ | CH₃ | CH₃ | H |
| 147 | CH₂CH₃ | CH₃ | OC(O)H | CH(CH₃)₂ | H | CH₃ | CH₃ | CH₃ |
| 148 | CH₂CH₃ | CH₃ | OC(O)H | CH(CH₃)₂ | CH₃ | H | CH₃ | CH₃ |
| 149 | CH₂CH₃ | CH₂CH₃ | OC(O)H | H | CH₃ | CH₃ | CH₃ | CH₃ |
| 150 | CH₂CH₃ | CH₂CH₃ | OC(O)H | H | CH₃ | CH₃ | CH₂CH₃ | CH₃ |
| 151 | CH₂CH₃ | CH₂CH₃ | OC(O)H | H | CH₃ | CH₂CH₃ | CH₃ | CH₃ |
| 152 | CH₂CH₃ | CH₂CH₃ | OC(O)H | CH₃ | CH₃ | H | CH₃ | CH₃ |
| 153 | CH₂CH₃ | CH₂CH₃ | OC(O)H | CH₃ | CH₃ | H | CH₂CH₃ | CH₃ |
| 154 | CH₂CH₃ | CH₂CH₃ | OC(O)H | CH₃ | CH₃ | CH₃ | CH₃ | H |
| 155 | CH₂CH₃ | CH₂CH₃ | OC(O)H | CH₃ | CH₃ | CH₃ | CH₂CH₃ | H |
| 156 | CH₂CH₃ | CH₂CH₃ | OC(O)H | CH₃ | CH₃ | CH₂CH₃ | CH₃ | H |
| 157 | CH₂CH₃ | CH₂CH₃ | OC(O)H | CH₂CH₃ | H | CH₃ | CH₃ | CH₃ |
| 158 | CH₂CH₃ | CH₂CH₃ | OC(O)H | CH₂CH₃ | CH₃ | H | CH₃ | CH₃ |
| 159 | CH₂CH₃ | CH₂CH₃ | OC(O)H | CH₂CH₃ | CH₃ | CH₃ | CH₃ | H |
| 160 | CH₂CH₃ | CH₂CH₃ | OC(O)H | CH(CH₃)₂ | H | CH₃ | CH₃ | CH₃ |
| 161 | CH₂CH₃ | CH₂CH₃ | OC(O)H | CH(CH₃)₂ | CH₃ | H | CH₃ | CH₃ |
| 162 | CH₂CH₃ | OC(O)H | H | H | CH₃ | CH₃ | CH₃ | CH₃ |
| 163 | CH₂CH₃ | OC(O)H | H | H | CH₃ | CH₃ | CH₂CH₃ | CH₃ |
| 164 | CH₂CH₃ | OC(O)H | H | H | CH₃ | CH₂CH₃ | CH₃ | CH₃ |
| 165 | CH₂CH₃ | OC(O)H | H | CH₃ | CH₃ | H | CH₃ | CH₃ |
| 166 | CH₂CH₃ | OC(O)H | H | CH₃ | CH₃ | H | CH₂CH₃ | CH₃ |
| 167 | CH₂CH₃ | OC(O)H | H | CH₃ | CH₃ | CH₃ | CH₃ | H |
| 168 | CH₂CH₃ | OC(O)H | H | CH₃ | CH₃ | CH₃ | CH₂CH₃ | H |
| 169 | CH₂CH₃ | OC(O)H | H | CH₃ | CH₃ | CH₂CH₃ | CH₃ | H |
| 170 | CH₂CH₃ | OC(O)H | H | CH₂CH₃ | H | CH₃ | CH₃ | CH₃ |
| 171 | CH₂CH₃ | OC(O)H | H | CH₂CH₃ | CH₃ | H | CH₃ | CH₃ |
| 172 | CH₂CH₃ | OC(O)H | H | CH₂CH₃ | CH₃ | CH₃ | CH₃ | H |
| 173 | CH₂CH₃ | OC(O)H | H | CH(CH₃)₂ | H | CH₃ | CH₃ | CH₃ |
| 174 | CH₂CH₃ | OC(O)H | H | CH(CH₃)₂ | CH₃ | H | CH₃ | CH₃ |
| 175 | CH₂CH₃ | OC(O)H | CH₃ | H | CH₃ | CH₃ | CH₃ | CH₃ |
| 176 | CH₂CH₃ | OC(O)H | CH₃ | H | CH₃ | CH₃ | CH₂CH₃ | CH₃ |
| 177 | CH₂CH₃ | OC(O)H | CH₃ | H | CH₃ | CH₂CH₃ | CH₃ | CH₃ |
| 178 | CH₂CH₃ | OC(O)H | CH₃ | CH₃ | CH₃ | H | CH₃ | CH₃ |
| 179 | CH₂CH₃ | OC(O)H | CH₃ | CH₃ | CH₃ | H | CH₂CH₃ | CH₃ |
| 180 | CH₂CH₃ | OC(O)H | CH₃ | CH₃ | CH₃ | CH₃ | CH₃ | H |
| 181 | CH₂CH₃ | OC(O)H | CH₃ | CH₃ | CH₃ | CH₃ | CH₂CH₃ | H |
| 182 | CH₂CH₃ | OC(O)H | CH₃ | CH₃ | CH₃ | CH₂CH₃ | CH₃ | H |
| 183 | CH₂CH₃ | OC(O)H | CH₃ | CH₂CH₃ | H | CH₃ | CH₃ | CH₃ |
| 184 | CH₂CH₃ | OC(O)H | CH₃ | CH₂CH₃ | CH₃ | H | CH₃ | CH₃ |
| 185 | CH₂CH₃ | OC(O)H | CH₃ | CH₂CH₃ | CH₃ | CH₃ | CH₃ | H |
| 186 | CH₂CH₃ | OC(O)H | CH₃ | CH(CH₃)₂ | H | CH₃ | CH₃ | CH₃ |
| 187 | CH₂CH₃ | OC(O)H | CH₃ | CH(CH₃)₂ | CH₃ | H | CH₃ | CH₃ |
| 188 | CH₂CH₃ | OC(O)H | CH₂CH₃ | H | CH₃ | CH₃ | CH₃ | CH₃ |
| 189 | CH₂CH₃ | OC(O)H | CH₂CH₃ | H | CH₃ | CH₃ | CH₂CH₃ | CH₃ |
| 190 | CH₂CH₃ | OC(O)H | CH₂CH₃ | H | CH₃ | CH₂CH₃ | CH₃ | CH₃ |
| 191 | CH₂CH₃ | OC(O)H | CH₂CH₃ | CH₃ | CH₃ | H | CH₃ | CH₃ |
| 192 | CH₂CH₃ | OC(O)H | CH₂CH₃ | CH₃ | CH₃ | H | CH₂CH₃ | CH₃ |
| 193 | CH₂CH₃ | OC(O)H | CH₂CH₃ | CH₃ | CH₃ | CH₃ | CH₃ | H |
| 194 | CH₂CH₃ | OC(O)H | CH₂CH₃ | CH₃ | CH₃ | CH₃ | CH₂CH₃ | H |
| 195 | CH₂CH₃ | OC(O)H | CH₂CH₃ | CH₃ | CH₃ | CH₂CH₃ | CH₃ | H |
| 196 | CH₂CH₃ | OC(O)H | CH₂CH₃ | CH₂CH₃ | H | CH₃ | CH₃ | CH₃ |
| 197 | CH₂CH₃ | OC(O)H | CH₂CH₃ | CH₂CH₃ | CH₃ | H | CH₃ | CH₃ |
| 198 | CH₂CH₃ | OC(O)H | CH₂CH₃ | CH₂CH₃ | CH₃ | CH₃ | CH₃ | H |
| 199 | CH₂CH₃ | OC(O)H | CH₂CH₃ | CH(CH₃)₂ | H | CH₃ | CH₃ | CH₃ |
| 200 | CH₂CH₃ | OC(O)H | CH₂CH₃ | CH(CH₃)₂ | CH₃ | H | CH₃ | CH₃ |
| 201 | OCH₃ | H | OC(O)H | H | CH₃ | CH₃ | CH₃ | CH₃ |
| 202 | OCH₃ | H | OC(O)H | H | CH₃ | CH₃ | CH₂CH₃ | CH₃ |
| 203 | OCH₃ | H | OC(O)H | H | CH₃ | CH₂CH₃ | CH₃ | CH₃ |
| 204 | OCH₃ | H | OC(O)H | CH₃ | CH₃ | H | CH₃ | CH₃ |
| 205 | OCH₃ | H | OC(O)H | CH₃ | CH₃ | H | CH₂CH₃ | CH₃ |
| 206 | OCH₃ | H | OC(O)H | CH₃ | CH₃ | CH₃ | CH₃ | H |
| 207 | OCH₃ | H | OC(O)H | CH₃ | CH₃ | CH₃ | CH₂CH₃ | H |
| 208 | OCH₃ | H | OC(O)H | CH₃ | CH₃ | CH₂CH₃ | CH₃ | H |
| 209 | OCH₃ | H | OC(O)H | CH₂CH₃ | H | CH₃ | CH₃ | CH₃ |
| 210 | OCH₃ | H | OC(O)H | CH₂CH₃ | CH₃ | H | CH₃ | CH₃ |
| 211 | OCH₃ | H | OC(O)H | CH₂CH₃ | CH₃ | CH₃ | CH₃ | H |
| 212 | OCH₃ | H | OC(O)H | CH(CH₃)₂ | H | CH₃ | CH₃ | CH₃ |

TABLE I-continued

| Compound | R¹ | R² | R³ | R⁴ | R⁵ | R⁶ | R⁷ | R⁸ |
|---|---|---|---|---|---|---|---|---|
| 213 | OCH₃ | H | OC(O)H | CH(CH₃)₂ | CH₃ | H | CH₃ | CH₃ |
| 214 | OCH₃ | CH₃ | OC(O)H | H | CH₃ | CH₃ | CH₃ | CH₃ |
| 215 | OCH₃ | CH₃ | OC(O)H | H | CH₃ | CH₃ | CH₂CH₃ | CH₃ |
| 216 | OCH₃ | CH₃ | OC(O)H | H | CH₃ | CH₂CH₃ | CH₃ | CH₃ |
| 217 | OCH₃ | CH₃ | OC(O)H | CH₃ | CH₃ | H | CH₃ | CH₃ |
| 218 | OCH₃ | CH₃ | OC(O)H | CH₃ | CH₃ | H | CH₂CH₃ | CH₃ |
| 219 | OCH₃ | CH₃ | OC(O)H | CH₃ | CH₃ | CH₃ | CH₃ | H |
| 220 | OCH₃ | CH₃ | OC(O)H | CH₃ | CH₃ | CH₃ | CH₂CH₃ | H |
| 221 | OCH₃ | CH₃ | OC(O)H | CH₃ | CH₃ | CH₂CH₃ | CH₃ | H |
| 222 | OCH₃ | CH₃ | OC(O)H | CH₂CH₃ | H | CH₃ | CH₃ | CH₃ |
| 223 | OCH₃ | CH₃ | OC(O)H | CH₂CH₃ | CH₃ | H | CH₃ | CH₃ |
| 224 | OCH₃ | CH₃ | OC(O)H | CH₂CH₃ | CH₃ | CH₃ | CH₃ | H |
| 225 | OCH₃ | CH₃ | OC(O)H | CH(CH₃)₂ | H | CH₃ | CH₃ | CH₃ |
| 226 | OCH₃ | CH₂CH₃ | OC(O)H | CH(CH₃)₂ | CH₃ | H | CH₃ | CH₃ |
| 227 | OCH₃ | CH₂CH₃ | OC(O)H | H | CH₃ | CH₃ | CH₃ | CH₃ |
| 228 | OCH₃ | CH₂CH₃ | OC(O)H | H | CH₃ | CH₃ | CH₂CH₃ | CH₃ |
| 229 | OCH₃ | CH₂CH₃ | OC(O)H | H | CH₃ | CH₂CH₃ | CH₃ | CH₃ |
| 230 | OCH₃ | CH₂CH₃ | OC(O)H | CH₃ | CH₃ | H | CH₃ | CH₃ |
| 231 | OCH₃ | CH₂CH₃ | OC(O)H | CH₃ | CH₃ | H | CH₂CH₃ | CH₃ |
| 232 | OCH₃ | CH₂CH₃ | OC(O)H | CH₃ | CH₃ | CH₃ | CH₃ | H |
| 233 | OCH₃ | CH₂CH₃ | OC(O)H | CH₃ | CH₃ | CH₃ | CH₂CH₃ | H |
| 234 | OCH₃ | CH₂CH₃ | OC(O)H | CH₃ | CH₃ | CH₂CH₃ | CH₃ | H |
| 235 | OCH₃ | CH₂CH₃ | OC(O)H | CH₂CH₃ | H | CH₃ | CH₃ | CH₃ |
| 236 | OCH₃ | CH₂CH₃ | OC(O)H | CH₂CH₃ | CH₃ | H | CH₃ | CH₃ |
| 237 | OCH₃ | CH₂CH₃ | OC(O)H | CH₂CH₃ | CH₃ | CH₃ | CH₃ | H |
| 238 | OCH₃ | CH₂CH₃ | OC(O)H | CH(CH₃)₂ | H | CH₃ | CH₃ | CH₃ |
| 239 | OCH₃ | CH₂CH₃ | OC(O)H | CH(CH₃)₂ | CH₃ | H | CH₃ | CH₃ |
| 240 | OCH₃ | OC(O)H | H | H | CH₃ | CH₃ | CH₃ | CH₃ |
| 241 | OCH₃ | OC(O)H | H | H | CH₃ | CH₃ | CH₂CH₃ | CH₃ |
| 242 | OCH₃ | OC(O)H | H | H | CH₃ | CH₂CH₃ | CH₃ | CH₃ |
| 243 | OCH₃ | OC(O)H | H | CH₃ | CH₃ | H | CH₃ | CH₃ |
| 244 | OCH₃ | OC(O)H | H | CH₃ | CH₃ | H | CH₂CH₃ | CH₃ |
| 245 | OCH₃ | OC(O)H | H | CH₃ | CH₃ | CH₃ | CH₃ | H |
| 246 | OCH₃ | OC(O)H | H | CH₃ | CH₃ | CH₃ | CH₂CH₃ | H |
| 247 | OCH₃ | OC(O)H | H | CH₃ | CH₃ | CH₂CH₃ | CH₃ | H |
| 248 | OCH₃ | OC(O)H | H | CH₂CH₃ | H | CH₃ | CH₃ | CH₃ |
| 249 | OCH₃ | OC(O)H | H | CH₂CH₃ | CH₃ | H | CH₃ | CH₃ |
| 250 | OCH₃ | OC(O)H | H | CH₂CH₃ | CH₃ | CH₃ | CH₃ | H |
| 251 | OCH₃ | OC(O)H | H | CH(CH₃)₂ | H | CH₃ | CH₃ | CH₃ |
| 252 | OCH₃ | OC(O)H | H | CH(CH₃)₂ | CH₃ | H | CH₃ | CH₃ |
| 253 | OCH₃ | OC(O)H | CH₃ | H | CH₃ | CH₃ | CH₃ | CH₃ |
| 254 | OCH₃ | OC(O)H | CH₃ | H | CH₃ | CH₃ | CH₂CH₃ | CH₃ |
| 255 | OCH₃ | OC(O)H | CH₃ | H | CH₃ | CH₂CH₃ | CH₃ | CH₃ |
| 256 | OCH₃ | OC(O)H | CH₃ | CH₃ | CH₃ | H | CH₃ | CH₃ |
| 257 | OCH₃ | OC(O)H | CH₃ | CH₃ | CH₃ | H | CH₂CH₃ | CH₃ |
| 258 | OCH₃ | OC(O)H | CH₃ | CH₃ | CH₃ | CH₃ | CH₃ | H |
| 259 | OCH₃ | OC(O)H | CH₃ | CH₃ | CH₃ | CH₃ | CH₂CH₃ | H |
| 260 | OCH₃ | OC(O)H | CH₃ | CH₃ | CH₃ | CH₂CH₃ | CH₃ | H |
| 261 | OCH₃ | OC(O)H | CH₃ | CH₂CH₃ | H | CH₃ | CH₃ | CH₃ |
| 262 | OCH₃ | OC(O)H | CH₃ | CH₂CH₃ | CH₃ | H | CH₃ | CH₃ |
| 263 | OCH₃ | OC(O)H | CH₃ | CH₂CH₃ | CH₃ | CH₃ | CH₃ | H |
| 264 | OCH₃ | OC(O)H | CH₃ | CH(CH₃)₂ | H | CH₃ | CH₃ | CH₃ |
| 265 | OCH₃ | OC(O)H | CH₃ | CH(CH₃)₂ | CH₃ | H | CH₃ | CH₃ |
| 266 | OCH₃ | OC(O)H | CH₂CH₃ | H | CH₃ | CH₃ | CH₃ | CH₃ |
| 267 | OCH₃ | OC(O)H | CH₂CH₃ | H | CH₃ | CH₃ | CH₂CH₃ | CH₃ |
| 268 | OCH₃ | OC(O)H | CH₂CH₃ | H | CH₃ | CH₂CH₃ | CH₃ | CH₃ |
| 269 | OCH₃ | OC(O)H | CH₂CH₃ | CH₃ | CH₃ | H | CH₃ | CH₃ |
| 270 | OCH₃ | OC(O)H | CH₂CH₃ | CH₃ | CH₃ | H | CH₂CH₃ | CH₃ |
| 271 | OCH₃ | OC(O)H | CH₂CH₃ | CH₃ | CH₃ | CH₃ | CH₃ | H |
| 272 | OCH₃ | OC(O)H | CH₂CH₃ | CH₃ | CH₃ | CH₃ | CH₂CH₃ | H |
| 273 | OCH₃ | OC(O)H | CH₂CH₃ | CH₃ | CH₃ | CH₂CH₃ | CH₃ | H |
| 274 | OCH₃ | OC(O)H | CH₂CH₃ | CH₂CH₃ | H | CH₃ | CH₃ | CH₃ |
| 275 | OCH₃ | OC(O)H | CH₂CH₃ | CH₂CH₃ | CH₃ | H | CH₃ | CH₃ |
| 276 | OCH₃ | OC(O)H | CH₂CH₃ | CH₂CH₃ | CH₃ | CH₃ | CH₃ | H |
| 277 | OCH₃ | OC(O)H | CH₂CH₃ | CH(CH₃)₂ | H | CH₃ | CH₃ | CH₃ |
| 278 | OCH₃ | OC(O)H | CH₂CH₃ | CH(CH₃)₂ | CH₃ | H | CH₃ | CH₃ |
| 279 | OH | H | OC(O)H | H | CH₃ | CH₃ | CH₃ | CH₃ |
| 280 | OH | H | OC(O)H | H | CH₃ | CH₃ | CH₂CH₃ | CH₃ |
| 281 | OH | H | OC(O)H | H | CH₃ | CH₂CH₃ | CH₃ | CH₃ |
| 282 | OH | H | OC(O)H | CH₃ | CH₃ | H | CH₃ | CH₃ |
| 283 | OH | H | OC(O)H | CH₃ | CH₃ | H | CH₂CH₃ | CH₃ |
| 284 | OH | H | OC(O)H | CH₃ | CH₃ | CH₃ | CH₃ | H |
| 285 | OH | H | OC(O)H | CH₃ | CH₃ | CH₃ | CH₂CH₃ | H |
| 286 | OH | H | OC(O)H | CH₃ | CH₃ | CH₂CH₃ | CH₃ | H |
| 287 | OH | H | OC(O)H | CH₂CH₃ | H | CH₃ | CH₃ | CH₃ |
| 288 | OH | H | OC(O)H | CH₂CH₃ | CH₃ | H | CH₃ | CH₃ |
| 289 | OH | H | OC(O)H | CH₂CH₃ | CH₃ | CH₃ | CH₃ | H |
| 290 | OH | H | OC(O)H | CH(CH₃)₂ | H | CH₃ | CH₃ | CH₃ |
| 291 | OH | H | OC(O)H | CH(CH₃)₂ | CH₃ | H | CH₃ | CH₃ |
| 292 | OH | CH₃ | OC(O)H | H | CH₃ | CH₃ | CH₃ | CH₃ |
| 293 | OH | CH₃ | OC(O)H | H | CH₃ | CH₃ | CH₂CH₃ | CH₃ |

TABLE I-continued

| Compound | R¹ | R² | R³ | R⁴ | R⁵ | R⁶ | R⁷ | R⁸ |
|---|---|---|---|---|---|---|---|---|
| 294 | OH | CH₃ | OC(O)H | H | CH₃ | CH₂CH₃ | CH₃ | CH₃ |
| 295 | OH | CH₃ | OC(O)H | CH₃ | CH₃ | H | CH₃ | CH₃ |
| 296 | OH | CH₃ | OC(O)H | H | CH₃ | H | CH₂CH₃ | CH₃ |
| 297 | OH | CH₃ | OC(O)H | CH₃ | CH₃ | CH₃ | CH₃ | H |
| 298 | OH | CH₃ | OC(O)H | CH₃ | CH₃ | CH₃ | CH₂CH₃ | H |
| 299 | OH | CH₃ | OC(O)H | CH₃ | CH₃ | CH₂CH₃ | CH₃ | H |
| 300 | OH | CH₃ | OC(O)H | CH₂CH₃ | H | CH₃ | CH₃ | CH₃ |
| 301 | OH | CH₃ | OC(O)H | CH₂CH₃ | CH₃ | H | CH₃ | CH₃ |
| 302 | OH | CH₃ | OC(O)H | CH₂CH₃ | CH₃ | CH₃ | CH₃ | H |
| 303 | OH | CH₃ | OC(O)H | CH(CH₃)₂ | H | CH₃ | CH₃ | CH₃ |
| 304 | OH | CH₃ | OC(O)H | CH(CH₃)₂ | CH₃ | H | CH₃ | CH₃ |
| 305 | OH | CH₂CH₃ | OC(O)H | H | CH₃ | CH₃ | CH₃ | CH₃ |
| 306 | OH | CH₂CH₃ | OC(O)H | H | CH₃ | CH₃ | CH₂CH₃ | CH₃ |
| 307 | OH | CH₂CH₃ | OC(O)H | H | CH₃ | CH₂CH₃ | CH₃ | CH₃ |
| 308 | OH | CH₂CH₃ | OC(O)H | CH₃ | CH₃ | H | CH₃ | CH₃ |
| 309 | OH | CH₂CH₃ | OC(O)H | CH₃ | CH₃ | H | CH₂CH₃ | CH₃ |
| 310 | OH | CH₂CH₃ | OC(O)H | CH₃ | CH₃ | CH₃ | CH₃ | H |
| 311 | OH | CH₂CH₃ | OC(O)H | CH₃ | CH₃ | CH₃ | CH₂CH₃ | H |
| 312 | OH | CH₂CH₃ | OC(O)H | CH₃ | CH₃ | CH₂CH₃ | CH₃ | H |
| 313 | OH | CH₂CH₃ | OC(O)H | CH₂CH₃ | H | CH₃ | CH₃ | CH₃ |
| 314 | OH | CH₂CH₃ | OC(O)H | CH₂CH₃ | CH₃ | H | CH₃ | CH₃ |
| 315 | OH | CH₂CH₃ | OC(O)H | CH₂CH₃ | CH₃ | CH₃ | CH₃ | H |
| 316 | OH | CH₂CH₃ | OC(O)H | CH(CH₃)₂ | H | CH₃ | CH₃ | CH₃ |
| 317 | OH | CH₂CH₃ | OC(O)H | CH(CH₃)₂ | CH₃ | H | CH₃ | CH₃ |
| 318 | OH | OC(O)H | H | H | CH₃ | CH₃ | CH₃ | CH₃ |
| 319 | OH | OC(O)H | H | H | CH₃ | CH₃ | CH₂CH₃ | CH₃ |
| 320 | OH | OC(O)H | H | H | CH₃ | CH₂CH₃ | CH₃ | CH₃ |
| 321 | OH | OC(O)H | H | CH₃ | CH₃ | H | CH₃ | CH₃ |
| 322 | OH | OC(O)H | H | CH₃ | CH₃ | H | CH₂CH₃ | CH₃ |
| 323 | OH | OC(O)H | H | CH₃ | CH₃ | CH₃ | CH₃ | H |
| 324 | OH | OC(O)H | H | CH₃ | CH₃ | CH₃ | CH₂CH₃ | H |
| 325 | OH | OC(O)H | H | CH₃ | CH₃ | CH₂CH₃ | CH₃ | H |
| 326 | OH | OC(O)H | H | CH₂CH₃ | H | CH₃ | CH₃ | CH₃ |
| 327 | OH | OC(O)H | H | CH₂CH₃ | CH₃ | H | CH₃ | CH₃ |
| 328 | OH | OC(O)H | H | CH₂CH₃ | CH₃ | CH₃ | CH₃ | H |
| 329 | OH | OC(O)H | H | CH(CH₃)₂ | H | CH₃ | CH₃ | CH₃ |
| 330 | OH | OC(O)H | H | CH(CH₃)₂ | CH₃ | H | CH₃ | CH₃ |
| 331 | OH | OC(O)H | CH₃ | H | CH₃ | CH₃ | CH₃ | CH₃ |
| 332 | OH | OC(O)H | CH₃ | H | CH₃ | CH₃ | CH₂CH₃ | CH₃ |
| 333 | OH | OC(O)H | CH₃ | H | CH₃ | CH₂CH₃ | CH₃ | CH₃ |
| 334 | OH | OC(O)H | CH₃ | CH₃ | CH₃ | H | CH₃ | CH₃ |
| 335 | OH | OC(O)H | CH₃ | CH₃ | CH₃ | H | CH₂CH₃ | CH₃ |
| 336 | OH | OC(O)H | CH₃ | CH₃ | CH₃ | CH₃ | CH₃ | H |
| 337 | OH | OC(O)H | CH₃ | CH₃ | CH₃ | CH₃ | CH₂CH₃ | H |
| 338 | OH | OC(O)H | CH₃ | CH₃ | CH₃ | CH₂CH₃ | CH₃ | H |
| 339 | OH | OC(O)H | CH₃ | CH₂CH₃ | H | CH₃ | CH₃ | CH₃ |
| 340 | OH | OC(O)H | CH₃ | CH₂CH₃ | CH₃ | H | CH₃ | CH₃ |
| 341 | OH | OC(O)H | CH₃ | CH₂CH₃ | CH₃ | CH₃ | CH₃ | H |
| 342 | OH | OC(O)H | CH₃ | CH(CH₃)₂ | H | CH₃ | CH₃ | CH₃ |
| 343 | OH | OC(O)H | CH₃ | CH(CH₃)₂ | CH₃ | H | CH₃ | CH₃ |
| 344 | OH | OC(O)H | CH₂CH₃ | H | CH₃ | CH₃ | CH₃ | CH₃ |
| 345 | OH | OC(O)H | CH₂CH₃ | H | CH₃ | CH₃ | CH₂CH₃ | CH₃ |
| 346 | OH | OC(O)H | CH₂CH₃ | H | CH₃ | CH₂CH₃ | CH₃ | CH₃ |
| 347 | OH | OC(O)H | CH₂CH₃ | CH₃ | H | CH₂CH₃ | CH₃ | CH₃ |
| 348 | OH | OC(O)H | CH₂CH₃ | CH₃ | CH₃ | H | CH₃ | CH₃ |
| 349 | OH | OC(O)H | CH₂CH₃ | CH₃ | CH₃ | H | CH₂CH₃ | CH₃ |
| 350 | OH | OC(O)H | CH₂CH₃ | CH₃ | CH₃ | CH₃ | CH₃ | H |
| 351 | OH | OC(O)H | CH₂CH₃ | CH₃ | CH₃ | CH₃ | CH₂CH₃ | H |
| 352 | OH | OC(O)H | CH₂CH₃ | CH₃ | CH₃ | CH₂CH₃ | CH₃ | H |
| 353 | OH | OC(O)H | CH₂CH₃ | CH₂CH₃ | H | CH₃ | CH₃ | CH₃ |
| 354 | OH | OC(O)H | CH₂CH₃ | CH₂CH₃ | CH₃ | H | CH₃ | CH₃ |
| 355 | OH | OC(O)H | CH₂CH₃ | CH₂CH₃ | CH₃ | CH₃ | CH₃ | H |
| 356 | OH | OC(O)H | CH₂CH₃ | CH(CH₃)₂ | H | CH₃ | CH₃ | CH₃ |
| 357 | OH | OC(O)H | CH₂CH₃ | CH(CH₃)₂ | CH₃ | H | CH₃ | CH₃ |
| 358 | CH₃ | OCH₃ | OC(O)H | H | CH₃ | CH₃ | CH₃ | CH₃ |
| 359 | CH₃ | OCH₃ | OC(O)H | H | CH₃ | CH₃ | CH₂CH₃ | CH₃ |
| 360 | CH₃ | OCH₃ | OC(O)H | H | CH₃ | CH₃ | CH₂CH₃ | CH₃ |
| 361 | CH₃ | OCH₃ | OC(O)H | CH₃ | CH₃ | H | CH₃ | CH₃ |
| 362 | CH₃ | OCH₃ | OC(O)H | CH₃ | CH₃ | H | CH₂CH₃ | CH₃ |
| 363 | CH₃ | OCH₃ | OC(O)H | CH₃ | CH₃ | CH₃ | CH₃ | H |
| 364 | CH₃ | OCH₃ | OC(O)H | CH₃ | CH₃ | CH₃ | CH₂CH₃ | H |
| 365 | CH₃ | OCH₃ | OC(O)H | CH₃ | CH₃ | CH₂CH₃ | CH₃ | H |
| 366 | CH₃ | OCH₃ | OC(O)H | CH₂CH₃ | H | CH₃ | CH₃ | CH₃ |
| 367 | CH₃ | OCH₃ | OC(O)H | CH₂CH₃ | CH₃ | H | CH₃ | CH₃ |
| 368 | CH₃ | OCH₃ | OC(O)H | CH₂CH₃ | CH₃ | CH₃ | CH₃ | H |
| 369 | CH₃ | OCH₃ | OC(O)H | CH₂CH₃ | CH₃ | CH₃ | CH₃ | CH₃ |
| 370 | CH₃ | OCH₃ | OC(O)H | CH(CH₃)₂ | H | CH₃ | CH₃ | CH₃ |
| 371 | CH₃ | OCH₃ | OC(O)H | CH(CH₃)₂ | CH₃ | H | CH₃ | CH₃ |
| 372 | CH₃ | OH | OC(O)H | H | CH₃ | CH₃ | CH₃ | CH₃ |
| 373 | CH₃ | OH | OC(O)H | H | CH₃ | CH₂CH₃ | CH₃ | CH₃ |
| 374 | CH₃ | OH | OC(O)H | H | CH₃ | CH₃ | CH₂CH₃ | CH₃ |

TABLE I-continued

| Compound | R¹ | R² | R³ | R⁴ | R⁵ | R⁶ | R⁷ | R⁸ |
|---|---|---|---|---|---|---|---|---|
| 375 | CH₃ | OH | OC(O)H | CH₃ | CH₃ | H | CH₃ | CH₃ |
| 376 | CH₃ | OH | OC(O)H | CH₃ | CH₃ | H | CH₂CH₃ | CH₃ |
| 377 | CH₃ | OH | OC(O)H | CH₃ | CH₃ | CH₃ | CH₃ | H |
| 378 | CH₃ | OH | OC(O)H | CH₃ | CH₃ | CH₃ | CH₂CH₃ | H |
| 379 | CH₃ | OH | OC(O)H | CH₃ | CH₃ | CH₂CH₃ | CH₃ | H |
| 380 | CH₃ | OH | OC(O)H | CH₂CH₃ | H | CH₃ | CH₃ | CH₃ |
| 381 | CH₃ | OH | OC(O)H | CH₂CH₃ | CH₃ | H | CH₃ | CH₃ |
| 382 | CH₃ | OH | OC(O)H | CH₂CH₃ | CH₃ | CH₃ | CH₃ | H |
| 383 | CH₃ | OH | OC(O)H | CH₂CH₃ | CH₃ | CH₃ | CH₃ | CH₃ |
| 384 | CH₃ | OH | OC(O)H | CH(CH₃)₂ | H | CH₃ | CH₃ | CH₃ |
| 385 | CH₃ | OH | OC(O)H | CH(CH₃)₂ | CH₃ | H | CH₃ | CH₃ |
| 386 | CH₃ | OC(O)H | OCH₃ | H | CH₃ | CH₃ | CH₃ | CH₃ |
| 387 | CH₃ | OC(O)H | OCH₃ | H | CH₃ | CH₂CH₃ | CH₃ | CH₃ |
| 388 | CH₃ | OC(O)H | OCH₃ | H | CH₃ | CH₃ | CH₂CH₃ | CH₃ |
| 389 | CH₃ | OC(O)H | OCH₃ | CH₃ | CH₃ | H | CH₃ | CH₃ |
| 390 | CH₃ | OC(O)H | OCH₃ | CH₃ | CH₃ | H | CH₂CH₃ | CH₃ |
| 391 | CH₃ | OC(O)H | OCH₃ | CH₃ | CH₃ | CH₃ | CH₃ | H |
| 392 | CH₃ | OC(O)H | OCH₃ | CH₃ | CH₃ | CH₃ | CH₂CH₃ | H |
| 393 | CH₃ | OC(O)H | OCH₃ | CH₃ | CH₃ | CH₂CH₃ | CH₃ | H |
| 394 | CH₃ | OC(O)H | OCH₃ | CH₂CH₃ | H | CH₃ | CH₃ | CH₃ |
| 395 | CH₃ | OC(O)H | OCH₃ | CH₂CH₃ | CH₃ | H | CH₃ | CH₃ |
| 396 | CH₃ | OC(O)H | OCH₃ | CH₂CH₃ | CH₃ | CH₃ | CH₃ | H |
| 397 | CH₃ | OC(O)H | OCH₃ | CH₂CH₃ | CH₃ | CH₃ | CH₃ | CH₃ |
| 398 | CH₃ | OC(O)H | OCH₃ | CH(CH₃)₂ | H | CH₃ | CH₃ | CH₃ |
| 399 | CH₃ | OC(O)H | OCH₃ | CH(CH₃)₂ | CH₃ | H | CH₃ | CH₃ |
| 400 | CH₃ | OC(O)H | OH | H | CH₃ | CH₃ | CH₃ | CH₃ |
| 401 | CH₃ | OC(O)H | OH | H | CH₃ | CH₂CH₃ | CH₃ | CH₃ |
| 402 | CH₃ | OC(O)H | OH | H | CH₃ | CH₃ | CH₂CH₃ | CH₃ |
| 403 | CH₃ | OC(O)H | OH | CH₃ | CH₃ | H | CH₃ | CH₃ |
| 404 | CH₃ | OC(O)H | OH | CH₃ | CH₃ | H | CH₂CH₃ | CH₃ |
| 405 | CH₃ | OC(O)H | OH | CH₃ | CH₃ | CH₃ | CH₃ | H |
| 406 | CH₃ | OC(O)H | OH | CH₃ | CH₃ | CH₃ | CH₂CH₃ | H |
| 407 | CH₃ | OC(O)H | OH | CH₃ | CH₃ | CH₂CH₃ | CH₃ | H |
| 408 | CH₃ | OC(O)H | OH | CH₂CH₃ | H | CH₃ | CH₃ | CH₃ |
| 409 | CH₃ | OC(O)H | OH | CH₂CH₃ | CH₃ | H | CH₃ | CH₃ |
| 410 | CH₃ | OC(O)H | OH | CH₂CH₃ | CH₃ | CH₃ | CH₃ | H |
| 411 | CH₃ | OC(O)H | OH | CH₂CH₃ | CH₃ | CH₃ | CH₃ | CH₃ |
| 412 | CH₃ | OC(O)H | OH | CH(CH₃)₂ | H | CH₃ | CH₃ | CH₃ |
| 413 | CH₃ | OC(O)H | OH | CH(CH₃)₂ | CH₃ | H | CH₃ | CH₃ |
| 414 | CH₂CH₃ | OCH₃ | OC(O)H | H | CH₃ | CH₃ | CH₃ | CH₃ |
| 415 | CH₂CH₃ | OCH₃ | OC(O)H | H | CH₃ | CH₂CH₃ | CH₃ | CH₃ |
| 416 | CH₂CH₃ | OCH₃ | OC(O)H | H | CH₃ | CH₃ | CH₂CH₃ | CH₃ |
| 417 | CH₂CH₃ | OCH₃ | OC(O)H | CH₃ | CH₃ | H | CH₃ | CH₃ |
| 418 | CH₂CH₃ | OCH₃ | OC(O)H | CH₃ | CH₃ | H | CH₂CH₃ | CH₃ |
| 419 | CH₂CH₃ | OCH₃ | OC(O)H | CH₃ | CH₃ | CH₃ | CH₃ | H |
| 420 | CH₂CH₃ | OCH₃ | OC(O)H | CH₃ | CH₃ | CH₃ | CH₂CH₃ | H |
| 421 | CH₂CH₃ | OCH₃ | OC(O)H | CH₃ | CH₃ | CH₂CH₃ | CH₃ | H |
| 422 | CH₂CH₃ | OCH₃ | OC(O)H | CH₂CH₃ | H | CH₃ | CH₃ | CH₃ |
| 423 | CH₂CH₃ | OCH₃ | OC(O)H | CH₂CH₃ | CH₃ | H | CH₃ | CH₃ |
| 424 | CH₂CH₃ | OCH₃ | OC(O)H | CH₂CH₃ | CH₃ | CH₃ | CH₃ | H |
| 425 | CH₂CH₃ | OCH₃ | OC(O)H | CH₂CH₃ | CH₃ | CH₃ | CH₃ | CH₃ |
| 426 | CH₂CH₃ | OCH₃ | OC(O)H | CH(CH₃)₂ | H | CH₃ | CH₃ | CH₃ |
| 427 | CH₂CH₃ | OCH₃ | OC(O)H | CH(CH₃)₂ | CH₃ | H | CH₃ | CH₃ |
| 428 | CH₂CH₃ | OH | OC(O)H | H | CH₃ | CH₃ | CH₃ | CH₃ |
| 429 | CH₂CH₃ | OH | OC(O)H | H | CH₃ | CH₂CH₃ | CH₃ | CH₃ |
| 430 | CH₂CH₃ | OH | OC(O)H | H | CH₃ | CH₃ | CH₂CH₃ | CH₃ |
| 431 | CH₂CH₃ | OH | OC(O)H | CH₃ | CH₃ | H | CH₃ | CH₃ |
| 432 | CH₂CH₃ | OH | OC(O)H | CH₃ | CH₃ | H | CH₂CH₃ | CH₃ |
| 433 | CH₂CH₃ | OH | OC(O)H | CH₃ | CH₃ | CH₃ | CH₃ | H |
| 434 | CH₂CH₃ | OH | OC(O)H | CH₃ | CH₃ | CH₃ | CH₂CH₃ | H |
| 435 | CH₂CH₃ | OH | OC(O)H | CH₃ | CH₃ | CH₂CH₃ | CH₃ | H |
| 436 | CH₂CH₃ | OH | OC(O)H | CH₂CH₃ | H | CH₃ | CH₃ | CH₃ |
| 437 | CH₂CH₃ | OH | OC(O)H | CH₂CH₃ | CH₃ | H | CH₃ | CH₃ |
| 438 | CH₂CH₃ | OH | OC(O)H | CH₂CH₃ | CH₃ | CH₃ | CH₃ | H |
| 439 | CH₂CH₃ | OH | OC(O)H | CH₂CH₃ | CH₃ | CH₃ | CH₃ | CH₃ |
| 440 | CH₂CH₃ | OH | OC(O)H | CH(CH₃)₂ | H | CH₃ | CH₃ | CH₃ |
| 441 | CH₂CH₃ | OH | OC(O)H | CH(CH₃)₂ | CH₃ | H | CH₃ | CH₃ |
| 442 | CH₂CH₃ | OC(O)H | OCH₃ | H | CH₃ | CH₃ | CH₃ | CH₃ |
| 443 | CH₂CH₃ | OC(O)H | OCH₃ | H | CH₃ | CH₂CH₃ | CH₃ | CH₃ |
| 444 | CH₂CH₃ | OC(O)H | OCH₃ | H | CH₃ | CH₃ | CH₂CH₃ | CH₃ |
| 445 | CH₂CH₃ | OC(O)H | OCH₃ | CH₃ | CH₃ | H | CH₃ | CH₃ |
| 446 | CH₂CH₃ | OC(O)H | OCH₃ | CH₃ | CH₃ | H | CH₂CH₃ | CH₃ |
| 447 | CH₂CH₃ | OC(O)H | OCH₃ | CH₃ | CH₃ | CH₃ | CH₃ | H |
| 448 | CH₂CH₃ | OC(O)H | OCH₃ | CH₃ | CH₃ | CH₃ | CH₂CH₃ | H |
| 449 | CH₂CH₃ | OC(O)H | OCH₃ | CH₃ | CH₃ | CH₂CH₃ | CH₃ | H |
| 450 | CH₂CH₃ | OC(O)H | OCH₃ | CH₂CH₃ | H | CH₃ | CH₃ | CH₃ |
| 451 | CH₂CH₃ | OC(O)H | OCH₃ | CH₂CH₃ | CH₃ | H | CH₃ | CH₃ |
| 452 | CH₂CH₃ | OC(O)H | OCH₃ | CH₂CH₃ | CH₃ | CH₃ | CH₃ | H |
| 453 | CH₂CH₃ | OC(O)H | OCH₃ | CH₂CH₃ | CH₃ | CH₃ | CH₃ | CH₃ |
| 454 | CH₂CH₃ | OC(O)H | OCH₃ | CH(CH₃)₂ | H | CH₃ | CH₃ | CH₃ |
| 455 | CH₂CH₃ | OC(O)H | OCH₃ | CH(CH₃)₂ | CH₃ | H | CH₃ | CH₃ |

TABLE I-continued

| Compound | R¹ | R² | R³ | R⁴ | R⁵ | R⁶ | R⁷ | R⁸ |
|---|---|---|---|---|---|---|---|---|
| 456 | CH₂CH₃ | OC(O)H | OH | H | CH₃ | CH₃ | CH₃ | CH₃ |
| 457 | CH₂CH₃ | OC(O)H | OH | H | CH₃ | CH₂CH₃ | CH₃ | CH₃ |
| 458 | CH₂CH₃ | OC(O)H | OH | H | CH₃ | CH₃ | CH₂CH₃ | CH₃ |
| 459 | CH₂CH₃ | OC(O)H | OH | CH₃ | CH₃ | H | CH₃ | CH₃ |
| 460 | CH₂CH₃ | OC(O)H | OH | CH₃ | CH₃ | H | CH₂CH₃ | CH₃ |
| 461 | CH₂CH₃ | OC(O)H | OH | CH₃ | CH₃ | CH₃ | CH₃ | H |
| 462 | CH₂CH₃ | OC(O)H | OH | CH₃ | CH₃ | CH₃ | CH₂CH₃ | H |
| 463 | CH₂CH₃ | OC(O)H | OH | CH₃ | CH₃ | CH₂CH₃ | CH₃ | H |
| 464 | CH₂CH₃ | OC(O)H | OH | CH₂CH₃ | H | CH₃ | CH₃ | CH₃ |
| 465 | CH₂CH₃ | OC(O)H | OH | CH₂CH₃ | CH₃ | H | CH₃ | CH₃ |
| 466 | CH₂CH₃ | OC(O)H | OH | CH₂CH₃ | CH₃ | CH₃ | CH₃ | H |
| 467 | CH₂CH₃ | OC(O)H | OH | CH₂CH₃ | CH₃ | CH₃ | CH₃ | CH₃ |
| 468 | CH₂CH₃ | OC(O)H | OH | CH(CH₃)₂ | H | CH₃ | CH₃ | CH₃ |
| 469 | CH₂CH₃ | OC(O)H | OH | CH(CH₃)₂ | CH₃ | H | CH₃ | CH₃ |
| 470 | OCH₃ | OCH₃ | OC(O)H | H | CH₃ | CH₃ | CH₃ | CH₃ |
| 471 | OCH₃ | OCH₃ | OC(O)H | H | CH₃ | CH₂CH₃ | CH₃ | CH₃ |
| 472 | OCH₃ | OCH₃ | OC(O)H | H | CH₃ | CH₃ | CH₂CH₃ | CH₃ |
| 473 | OCH₃ | OCH₃ | OC(O)H | CH₃ | CH₃ | H | CH₃ | CH₃ |
| 474 | OCH₃ | OCH₃ | OC(O)H | CH₃ | CH₃ | H | CH₂CH₃ | CH₃ |
| 475 | OCH₃ | OCH₃ | OC(O)H | CH₃ | CH₃ | CH₃ | CH₃ | H |
| 476 | OCH₃ | OCH₃ | OC(O)H | CH₃ | CH₃ | CH₃ | CH₂CH₃ | H |
| 477 | OCH₃ | OCH₃ | OC(O)H | CH₃ | CH₃ | CH₂CH₃ | CH₃ | H |
| 478 | OCH₃ | OCH₃ | OC(O)H | CH₂CH₃ | H | CH₃ | CH₃ | CH₃ |
| 479 | OCH₃ | OCH₃ | OC(O)H | CH₂CH₃ | CH₃ | H | CH₃ | CH₃ |
| 480 | OCH₃ | OCH₃ | OC(O)H | CH₂CH₃ | CH₃ | CH₃ | CH₃ | H |
| 481 | OCH₃ | OCH₃ | OC(O)H | CH₂CH₃ | CH₃ | CH₃ | CH₃ | CH₃ |
| 482 | OCH₃ | OCH₃ | OC(O)H | CH(CH₃)₂ | H | CH₃ | CH₃ | CH₃ |
| 483 | OCH₃ | OCH₃ | OC(O)H | CH(CH₃)₂ | CH₃ | H | CH₃ | CH₃ |
| 484 | OCH₃ | OC(O)H | OCH₃ | H | CH₃ | CH₃ | CH₃ | CH₃ |
| 485 | OCH₃ | OC(O)H | OCH₃ | H | CH₃ | CH₂CH₃ | CH₃ | CH₃ |
| 486 | OCH₃ | OC(O)H | OCH₃ | H | CH₃ | CH₃ | CH₂CH₃ | CH₃ |
| 487 | OCH₃ | OC(O)H | OCH₃ | CH₃ | CH₃ | H | CH₃ | CH₃ |
| 488 | OCH₃ | OC(O)H | OCH₃ | CH₃ | CH₃ | H | CH₂CH₃ | CH₃ |
| 489 | OCH₃ | OC(O)H | OCH₃ | CH₃ | CH₃ | CH₃ | CH₃ | H |
| 490 | OCH₃ | OC(O)H | OCH₃ | CH₃ | CH₃ | CH₃ | CH₂CH₃ | H |
| 491 | OCH₃ | OC(O)H | OCH₃ | CH₃ | CH₃ | CH₂CH₃ | CH₃ | H |
| 492 | OCH₃ | OC(O)H | OCH₃ | CH₂CH₃ | H | CH₃ | CH₃ | CH₃ |
| 493 | OCH₃ | OC(O)H | OCH₃ | CH₂CH₃ | CH₃ | H | CH₃ | CH₃ |
| 494 | OCH₃ | OC(O)H | OCH₃ | CH₂CH₃ | CH₃ | CH₃ | CH₃ | H |
| 495 | OCH₃ | OC(O)H | OCH₃ | CH₂CH₃ | CH₃ | CH₃ | CH₃ | CH₃ |
| 496 | OCH₃ | OC(O)H | OCH₃ | CH(CH₃)₂ | H | CH₃ | CH₃ | CH₃ |
| 497 | OCH₃ | OC(O)H | OCH₃ | CH(CH₃)₂ | CH₃ | H | CH₃ | CH₃ |
| 498 | H | H | OC(O)H | CH₃ | CH₃ | CH₃ | CH₃ | CH₃ |
| 499 | H | H | OC(O)H | CH₂CH₃ | CH₃ | CH₃ | CH₃ | CH₃ |
| 500 | H | H | OC(O)H | CH₃ | CH₃ | CH₂CH₃ | CH₃ | CH₃ |
| 501 | H | H | OC(O)H | CH₃ | CH₃ | CH₃ | CH₂CH₃ | CH₃ |
| 502 | H | CH₃ | OC(O)H | CH₃ | CH₃ | CH₃ | CH₃ | CH₃ |
| 503 | H | CH₃ | OC(O)H | CH₂CH₃ | CH₃ | CH₃ | CH₃ | CH₃ |
| 504 | H | CH₃ | OC(O)H | CH₃ | CH₃ | CH₂CH₃ | CH₃ | CH₃ |
| 505 | H | CH₃ | OC(O)H | CH₃ | CH₃ | CH₃ | CH₂CH₃ | CH₃ |
| 506 | H | CH₂CH₃ | OC(O)H | CH₃ | CH₃ | CH₃ | CH₃ | CH₃ |
| 507 | H | CH₂CH₃ | OC(O)H | CH₂CH₃ | CH₃ | CH₃ | CH₃ | CH₃ |
| 508 | H | CH₂CH₃ | OC(O)H | CH₃ | CH₃ | CH₂CH₃ | CH₃ | CH₃ |
| 509 | H | CH₂CH₃ | OC(O)H | CH₃ | CH₃ | CH₃ | CH₂CH₃ | CH₃ |
| 510 | CH₃ | H | OC(O)H | CH₃ | CH₃ | CH₃ | CH₃ | CH₃ |
| 511 | CH₃ | H | OC(O)H | CH₂CH₃ | CH₃ | CH₃ | CH₃ | CH₃ |
| 512 | CH₃ | H | OC(O)H | CH₃ | CH₃ | CH₂CH₃ | CH₃ | CH₃ |
| 513 | CH₃ | H | OC(O)H | CH₃ | CH₃ | CH₃ | CH₂CH₃ | CH₃ |
| 514 | CH₃ | CH₃ | OC(O)H | CH₃ | CH₃ | CH₃ | CH₃ | CH₃ |
| 515 | CH₃ | CH₃ | OC(O)H | CH₂CH₃ | CH₃ | CH₃ | CH₃ | CH₃ |
| 516 | CH₃ | CH₃ | OC(O)H | CH₃ | CH₃ | CH₂CH₃ | CH₃ | CH₃ |
| 517 | CH₃ | CH₃ | OC(O)H | CH₃ | CH₃ | CH₃ | CH₂CH₃ | CH₃ |
| 518 | CH₃ | CH₂CH₃ | OC(O)H | CH₃ | CH₃ | CH₃ | CH₃ | CH₃ |
| 519 | CH₃ | CH₂CH₃ | OC(O)H | CH₂CH₃ | CH₃ | CH₃ | CH₃ | CH₃ |
| 520 | CH₃ | CH₂CH₃ | OC(O)H | CH₃ | CH₃ | CH₂CH₃ | CH₃ | CH₃ |
| 521 | CH₃ | CH₂CH₃ | OC(O)H | CH₃ | CH₃ | CH₃ | CH₂CH₃ | CH₃ |
| 522 | CH₃ | CH₂CH₃ | OC(O)H | CH₃ | CH₃ | CH₃ | CH₃ | CH₃ |
| 523 | CH₃ | OCH₃ | OC(O)H | CH₃ | CH₃ | CH₂CH₃ | CH₃ | CH₃ |
| 524 | CH₃ | OCH₃ | OC(O)H | CH₃ | CH₃ | CH₃ | CH₂CH₃ | CH₃ |
| 525 | CH₃ | OCH₃ | OC(O)H | CH₃ | CH₃ | CH₃ | CH₃ | CH₃ |
| 526 | CH₃ | OCH₃ | OC(O)H | CH₃ | CH₃ | CH₂CH₃ | CH₃ | CH₃ |
| 527 | CH₃ | OCH₃ | OC(O)H | CH₃ | CH₃ | CH₃ | CH₂CH₃ | CH₃ |
| 528 | CH₂CH₃ | H | OC(O)H | CH₃ | CH₃ | CH₃ | CH₃ | CH₃ |
| 529 | CH₂CH₃ | H | OC(O)H | CH₂CH₃ | CH₃ | CH₃ | CH₃ | CH₃ |
| 530 | CH₂CH₃ | H | OC(O)H | CH₃ | CH₃ | CH₂CH₃ | CH₃ | CH₃ |
| 531 | CH₂CH₃ | H | OC(O)H | CH₃ | CH₃ | CH₃ | CH₂CH₃ | CH₃ |
| 532 | CH₂CH₃ | CH₃ | OC(O)H | CH₃ | CH₃ | CH₃ | CH₃ | CH₃ |
| 533 | CH₂CH₃ | CH₃ | OC(O)H | CH₂CH₃ | CH₃ | CH₃ | CH₃ | CH₃ |
| 534 | CH₂CH₃ | CH₃ | OC(O)H | CH₃ | CH₃ | CH₂CH₃ | CH₃ | CH₃ |
| 535 | CH₂CH₃ | CH₃ | OC(O)H | CH₃ | CH₃ | CH₃ | CH₂CH₃ | CH₃ |
| 536 | CH₂CH₃ | CH₂CH₃ | OC(O)H | CH₃ | CH₃ | CH₃ | CH₃ | CH₃ |

TABLE I-continued

| Compound | R¹ | R² | R³ | R⁴ | R⁵ | R⁶ | R⁷ | R⁸ |
|---|---|---|---|---|---|---|---|---|
| 537 | CH₂CH₃ | CH₂CH₃ | OC(O)H | CH₂CH₃ | CH₃ | CH₃ | CH₃ | CH₃ |
| 538 | CH₂CH₃ | CH₂CH₃ | OC(O)H | CH₃ | CH₃ | CH₂CH₃ | CH₃ | CH₃ |
| 539 | CH₂CH₃ | CH₂CH₃ | OC(O)H | CH₃ | CH₃ | CH₃ | CH₂CH₃ | CH₃ |
| 540 | CH₂CH₃ | OCH₃ | OC(O)H | CH₃ | CH₃ | CH₃ | CH₃ | CH₃ |
| 541 | CH₂CH₃ | OCH₃ | OC(O)H | CH₃ | CH₃ | CH₂CH₃ | CH₃ | CH₃ |
| 542 | CH₂CH₃ | OCH₃ | OC(O)H | CH₃ | CH₃ | CH₃ | CH₂CH₃ | CH₃ |
| 543 | CH₂CH₃ | OH | OC(O)H | CH₃ | CH₃ | CH₃ | CH₃ | CH₃ |
| 544 | CH₂CH₃ | OH | OC(O)H | CH₃ | CH₃ | CH₂CH₃ | CH₃ | CH₃ |
| 545 | CH₂CH₃ | OH | OC(O)H | CH₃ | CH₃ | CH₃ | CH₂CH₃ | CH₃ |
| 546 | OCH₃ | H | OC(O)H | CH₃ | CH₃ | CH₃ | CH₃ | CH₃ |
| 547 | OCH₃ | H | OC(O)H | CH₂CH₃ | CH₃ | CH₃ | CH₃ | CH₃ |
| 548 | OCH₃ | H | OC(O)H | CH₃ | CH₃ | CH₂CH₃ | CH₃ | CH₃ |
| 549 | OCH₃ | H | OC(O)H | CH₃ | CH₃ | CH₃ | CH₂CH₃ | CH₃ |
| 550 | OCH₃ | CH₃ | OC(O)H | CH₃ | CH₃ | CH₃ | CH₃ | CH₃ |
| 551 | OCH₃ | CH₃ | OC(O)H | CH₂CH₃ | CH₃ | CH₃ | CH₃ | CH₃ |
| 552 | OCH₃ | CH₃ | OC(O)H | CH₃ | CH₃ | CH₂CH₃ | CH₃ | CH₃ |
| 553 | OCH₃ | CH₃ | OC(O)H | CH₃ | CH₃ | CH₃ | CH₂CH₃ | CH₃ |
| 554 | OCH₃ | CH₂CH₃ | OC(O)H | CH₃ | CH₃ | CH₃ | CH₃ | CH₃ |
| 555 | OCH₃ | CH₂CH₃ | OC(O)H | CH₂CH₃ | CH₃ | CH₃ | CH₃ | CH₃ |
| 556 | OCH₃ | CH₂CH₃ | OC(O)H | CH₃ | CH₃ | CH₂CH₃ | CH₃ | CH₃ |
| 557 | OCH₃ | CH₂CH₃ | OC(O)H | CH₃ | CH₃ | CH₃ | CH₂CH₃ | CH₃ |
| 558 | OCH₃ | OCH₃ | OC(O)H | CH₃ | CH₃ | CH₃ | CH₃ | CH₃ |
| 559 | OCH₃ | OCH₃ | OC(O)H | CH₃ | CH₃ | CH₂CH₃ | CH₃ | CH₃ |
| 560 | OCH₃ | OCH₃ | OC(O)H | CH₃ | CH₃ | CH₃ | CH₂CH₃ | CH₃ |
| 561 | OH | H | OC(O)H | CH₃ | CH₃ | CH₃ | CH₃ | CH₃ |
| 562 | OH | H | OC(O)H | CH₂CH₃ | CH₃ | CH₃ | CH₃ | CH₃ |
| 563 | OH | H | OC(O)H | CH₃ | CH₃ | CH₂CH₃ | CH₃ | CH₃ |
| 564 | OH | H | OC(O)H | CH₃ | CH₃ | CH₃ | CH₂CH₃ | CH₃ |
| 565 | OH | CH₃ | OC(O)H | CH₃ | CH₃ | CH₃ | CH₃ | CH₃ |
| 566 | OH | CH₃ | OC(O)H | CH₂CH₃ | CH₃ | CH₃ | CH₃ | CH₃ |
| 567 | OH | CH₃ | OC(O)H | CH₃ | CH₃ | CH₂CH₃ | CH₃ | CH₃ |
| 568 | OH | CH₃ | OC(O)H | CH₃ | CH₃ | CH₃ | CH₂CH₃ | CH₃ |
| 569 | OH | CH₂CH₃ | OC(O)H | CH₃ | CH₃ | CH₃ | CH₃ | CH₃ |
| 570 | OH | CH₂CH₃ | OC(O)H | CH₂CH₃ | CH₃ | CH₃ | CH₃ | CH₃ |
| 571 | OH | CH₂CH₃ | OC(O)H | CH₃ | CH₃ | CH₂CH₃ | CH₃ | CH₃ |
| 572 | OH | CH₂CH₃ | OC(O)H | CH₃ | CH₃ | CH₃ | CH₂CH₃ | CH₃ |
| 573 | CH₃ | OC(O)H | H | CH₃ | CH₃ | CH₃ | CH₃ | CH₃ |
| 574 | CH₃ | OC(O)H | H | CH₂CH₃ | CH₃ | CH₃ | CH₃ | CH₃ |
| 575 | CH₃ | OC(O)H | H | CH₃ | CH₃ | CH₃ | CH₂CH₃ | CH₃ |
| 576 | CH₃ | OC(O)H | H | CH₃ | CH₃ | CH₃ | CH₂CH₃ | CH₃ |
| 577 | CH₃ | OC(O)H | CH₃ | CH₃ | CH₃ | CH₃ | CH₃ | CH₃ |
| 578 | CH₃ | OC(O)H | CH₃ | CH₂CH₃ | CH₃ | CH₃ | CH₃ | CH₃ |
| 579 | CH₃ | OC(O)H | CH₃ | CH₃ | CH₃ | CH₂CH₃ | CH₃ | CH₃ |
| 580 | CH₃ | OC(O)H | CH₃ | CH₃ | CH₃ | CH₃ | CH₂CH₃ | CH₃ |
| 581 | CH₃ | OC(O)H | CH₂CH₃ | CH₃ | CH₃ | CH₃ | CH₃ | CH₃ |
| 582 | CH₃ | OC(O)H | CH₂CH₃ | CH₂CH₃ | CH₃ | CH₃ | CH₃ | CH₃ |
| 583 | CH₃ | OC(O)H | CH₂CH₃ | CH₃ | CH₃ | CH₂CH₃ | CH₃ | CH₃ |
| 584 | CH₃ | OC(O)H | CH₂CH₃ | CH₃ | CH₃ | CH₃ | CH₂CH₃ | CH₃ |
| 585 | CH₂CH₃ | OC(O)H | H | CH₃ | CH₃ | CH₃ | CH₃ | CH₃ |
| 586 | CH₂CH₃ | OC(O)H | H | CH₂CH₃ | CH₃ | CH₃ | CH₃ | CH₃ |
| 587 | CH₂CH₃ | OC(O)H | H | CH₃ | CH₃ | CH₂CH₃ | CH₃ | CH₃ |
| 588 | CH₂CH₃ | OC(O)H | H | CH₃ | CH₃ | CH₃ | CH₂CH₃ | CH₃ |
| 589 | CH₂CH₃ | OC(O)H | CH₃ | CH₃ | CH₃ | CH₃ | CH₃ | CH₃ |
| 590 | CH₂CH₃ | OC(O)H | CH₃ | CH₂CH₃ | CH₃ | CH₃ | CH₃ | CH₃ |
| 591 | CH₂CH₃ | OC(O)H | CH₃ | CH₃ | CH₃ | CH₂CH₃ | CH₃ | CH₃ |
| 592 | CH₂CH₃ | OC(O)H | CH₃ | CH₃ | CH₃ | CH₃ | CH₂CH₃ | CH₃ |
| 593 | CH₂CH₃ | OC(O)H | CH₂CH₃ | CH₃ | CH₃ | CH₃ | CH₃ | CH₃ |
| 594 | CH₂CH₃ | OC(O)H | CH₂CH₃ | CH₂CH₃ | CH₃ | CH₃ | CH₃ | CH₃ |
| 595 | CH₂CH₃ | OC(O)H | CH₂CH₃ | CH₃ | CH₃ | CH₂CH₃ | CH₃ | CH₃ |
| 596 | CH₂CH₃ | OC(O)H | CH₂CH₃ | CH₃ | CH₃ | CH₃ | CH₂CH₃ | CH₃ |
| 597 | CH₂CH₃ | OC(O)H | OCH₃ | CH₃ | CH₃ | CH₃ | CH₃ | CH₃ |
| 598 | CH₂CH₃ | OC(O)H | OCH₃ | CH₃ | CH₃ | CH₂CH₃ | CH₃ | CH₃ |
| 599 | CH₂CH₃ | OC(O)H | OCH₃ | CH₃ | CH₃ | CH₃ | CH₂CH₃ | CH₃ |
| 600 | CH₂CH₃ | OC(O)H | OH | CH₃ | CH₃ | CH₃ | CH₃ | CH₃ |
| 601 | CH₂CH₃ | OC(O)H | OH | CH₃ | CH₃ | CH₂CH₃ | CH₃ | CH₃ |
| 602 | CH₂CH₃ | OC(O)H | OH | CH₃ | CH₃ | CH₃ | CH₂CH₃ | CH₃ |
| 603 | OCH₃ | OC(O)H | H | CH₃ | CH₃ | CH₃ | CH₃ | CH₃ |
| 604 | OCH₃ | OC(O)H | H | CH₂CH₃ | CH₃ | CH₃ | CH₃ | CH₃ |
| 605 | OCH₃ | OC(O)H | H | CH₃ | CH₃ | CH₂CH₃ | CH₃ | CH₃ |
| 606 | OCH₃ | OC(O)H | H | CH₃ | CH₃ | CH₃ | CH₂CH₃ | CH₃ |
| 607 | OCH₃ | OC(O)H | CH₃ | CH₃ | CH₃ | CH₃ | CH₃ | CH₃ |
| 608 | OCH₃ | OC(O)H | CH₃ | CH₂CH₃ | CH₃ | CH₃ | CH₃ | CH₃ |
| 609 | OCH₃ | OC(O)H | CH₃ | CH₃ | CH₃ | CH₂CH₃ | CH₃ | CH₃ |
| 610 | OCH₃ | OC(O)H | CH₃ | CH₃ | CH₃ | CH₃ | CH₂CH₃ | CH₃ |
| 611 | OCH₃ | OC(O)H | CH₂CH₃ | CH₃ | CH₃ | CH₃ | CH₃ | CH₃ |
| 612 | OCH₃ | OC(O)H | CH₂CH₃ | CH₂CH₃ | CH₃ | CH₃ | CH₃ | CH₃ |
| 613 | OCH₃ | OC(O)H | CH₂CH₃ | CH₃ | CH₃ | CH₂CH₃ | CH₃ | CH₃ |
| 614 | OCH₃ | OC(O)H | CH₂CH₃ | CH₃ | CH₃ | CH₃ | CH₂CH₃ | CH₃ |
| 615 | OCH₃ | OC(O)H | OCH₃ | CH₃ | CH₃ | CH₃ | CH₃ | CH₃ |
| 616 | OCH₃ | OC(O)H | OCH₃ | CH₃ | CH₃ | CH₂CH₃ | CH₃ | CH₃ |
| 617 | OCH₃ | OC(O)H | OCH₃ | CH₃ | CH₃ | CH₃ | CH₂CH₃ | CH₃ |

TABLE I-continued

| Compound | $R^1$ | $R^2$ | $R^3$ | $R^4$ | $R^5$ | $R^6$ | $R^7$ | $R^8$ |
|---|---|---|---|---|---|---|---|---|
| 618 | OH | OC(O)H | H | $CH_3$ | $CH_3$ | $CH_3$ | $CH_3$ | $CH_3$ |
| 619 | OH | OC(O)H | H | $CH_2CH_3$ | $CH_3$ | $CH_3$ | $CH_3$ | $CH_3$ |
| 620 | OH | OC(O)H | H | $CH_3$ | $CH_3$ | $CH_2CH_3$ | $CH_3$ | $CH_3$ |
| 621 | OH | OC(O)H | H | $CH_3$ | $CH_3$ | $CH_3$ | $CH_2CH_3$ | $CH_3$ |
| 622 | OH | OC(O)H | $CH_3$ | $CH_3$ | $CH_3$ | $CH_3$ | $CH_3$ | $CH_3$ |
| 623 | OH | OC(O)H | $CH_3$ | $CH_2CH_3$ | $CH_3$ | $CH_3$ | $CH_3$ | $CH_3$ |
| 624 | OH | OC(O)H | $CH_3$ | $CH_3$ | $CH_3$ | $CH_2CH_3$ | $CH_3$ | $CH_3$ |
| 625 | OH | OC(O)H | $CH_3$ | $CH_3$ | $CH_3$ | $CH_3$ | $CH_2CH_3$ | $CH_3$ |
| 626 | OH | OC(O)H | $CH_3$ | $CH_3$ | $CH_3$ | $CH_3$ | $CH(CH_3)_2$ | $CH_3$ |
| 627 | OH | OC(O)H | $CH_2CH_3$ | $CH_3$ | $CH_3$ | $CH_3$ | $CH_3$ | $CH_3$ |
| 628 | OH | OC(O)H | $CH_2CH_3$ | $CH_2CH_3$ | $CH_3$ | $CH_3$ | $CH_3$ | $CH_3$ |
| 629 | OH | OC(O)H | $CH_2CH_3$ | $CH_3$ | $CH_3$ | $CH_2CH_3$ | $CH_3$ | $CH_3$ |
| 630 | OH | OC(O)H | $CH_2CH_3$ | $CH_3$ | $CH_3$ | $CH_3$ | $CH_2CH_3$ | $CH_3$ |
| 631 | $CH_3$ | OC(O)H | $OCH_3$ | $CH_3$ | $CH_3$ | $CH_3$ | $CH_3$ | $CH_3$ |
| 632 | $CH_3$ | OC(O)H | $OCH_3$ | $CH_3$ | $CH_3$ | $CH_2CH_3$ | $CH_3$ | $CH_3$ |
| 633 | $CH_3$ | OC(O)H | $OCH_3$ | $CH_3$ | $CH_3$ | $CH_3$ | $CH_2CH_3$ | $CH_3$ |
| 634 | $CH_3$ | OC(O)H | OH | $CH_3$ | $CH_3$ | $CH_3$ | $CH_3$ | $CH_3$ |
| 635 | $CH_3$ | OC(O)H | OH | $CH_3$ | $CH_3$ | $CH_2CH_3$ | $CH_3$ | $CH_3$ |
| 636 | $CH_3$ | OC(O)H | OH | $CH_3$ | $CH_3$ | $CH_3$ | $CH_2CH_3$ | $CH_3$ |

The novel formate ester indane compounds of the present invention, with their musk aroma properties, have high utility in the fragrance industry. These compounds can be employed alone, in combination with one another, and/or in combination with one or more ingredients to provide excellent musk fragrance compositions. The compounds of the invention are particularly useful in rounding off compositions, and blend particularly well with aldehydes of various fragrance types.

For example, the compounds of Formula [I] may be used as olfactory components in anionic, cationic, non-ionic and zwitterionic detergents, soaps, fabric softener compositions, fabric softener articles for use in clothes dryers, space odorants and deodorants, perfumes, colognes, toilet water, toiletries, bath preparations, deodorants, cosmetics, hand lotions, sunscreens, powders, as well as in other ways. The amount of the subject compounds to be used in modifying the olfactory or fragrance properties of a composition (that is, modifying, augmenting, enhancing, or improving the aroma of such compositions), will vary depending upon the particular use intended, as will be readily apparent to those skilled in the art. Although they may be present in major or minor amounts, preferably, because of the strength of their odor, the compounds of the invention are generally employed as a minor ingredient, that is, in an amount of about 0.1 percent by weight of the fragrance composition up to about 50 percent by weight of the fragrance composition, preferably about 0.1 percent by weight up to about 30 percent by weight of the fragrance composition, and most preferably about 0.1 percent by weight up to about 5.0 percent by weight of the fragrance composition. Within these basic parameters, the olfactorily effective amount (that is, the amount of the compounds of Formula [I] effective to modify, augment, enhance or improve the aroma properties of a composition) will be well within the ambit of one skilled in the art, once armed with the present disclosures.

The fragrance compositions of the invention may, if desired, contain a carrier or vehicle (as used herein, the term "carrier" shall be considered synonymous with the term "vehicle"). Such carriers include liquids such as a non toxic alcohol, a non toxic glycol, or the like. An example of a non toxic alcohol is ethyl alcohol. An example of a non toxic glycol is 1,2-propylene glycol. Alternatively, the carrier can be an absorbent solid such as a gum, e.g., gum arabic, xantham gum or guar gum, or components for encapsulating a composition such as gelatin, by means of coacervation or such as a urea formaldehyde polymer whereby a polymeric shell is formed around a liquid perfume oil center. The amount of the vehicle or carrier will vary depending upon the particular vehicle or carrier employed and use intended, as will be readily apparent to those skilled in the art. However, the vehicle or carrier can generally be employed in an amount of about 5 percent by weight up to about 95 percent by weight of the fragrance composition.

The fragrance composition may alternatively or additionally contain other perfumery materials. Typical additional perfumery materials which may form part of compositions of the invention include: natural essential oils such as lemon oil, mandarin oil, clove leaf oil, petitgrain oil, cedar wood oil, patchouli oil, lavandin oil, neroli oil, ylang oil, rose absolute or jasmine absolute; natural resins such as labdanum resin or olibanum resin; single perfumery chemicals which may be isolated from natural sources or manufactures synthetically, as for example, alcohols such as geraniol, nerol, citronellol, linalol, tetrahydrogeraniol, $\beta$-phenylethyl alcohol, methyl phenyl carbinol, dimethyl benzyl carbinol, menthol or cedrol; acetates and other esters derived from such alcohols; aldehydes such as citral, citronellal, hydroxycitronellal, lauric aldehyde, undecylenic aldehyde, cinnamaldehyde, amyl cinnamic aldehyde, vanillin or heliotropin; acetals derived from such aldehydes; ketones such as methyl hexyl ketone, the ionones and the methylionones; phenolic compounds such as eugenol and isoeugenol; other synthetic musks such as musk xylene, musk ketone, hexamethylisochroman, 5-acetylisopropyletramethylindane, 6-acetyl-hexamethyl-tetralin (TETRALIDE®,a registered trademark of Bush Boake Allen Limited), 5-acetyl-hexamethylindane and ethylene brassylate; and other materials commonly employed in the art of perfumery. Typically at least five, and usually at least ten, of such materials will be present as components of the active ingredient. The amount of the additional perfumery material will vary depending upon the particular perfumery material employed and use intended, as will be apparent to those skilled in the art.

Fragrance compositions and preparatory techniques are well known in the art, and are disclosed, for example, in "Soap, Perfumery and Cosmetics", by W.A. Poucher, 7th edition, published by Chapman & Hall (London) (1959); "Perfume and Flavour Chemicals", by S. Arctander, published by the author (Montclair) (1959); and "Perfume and Flavour Materials of Natural Origin", also by S. Arctander, self-published (Elizabeth, N.J.) (1960), the disclosures of each of which are incorporated herein by reference, in their entirety.

The invention is further described in the following Examples 1–11, which are prophetic examples illustrating methods of preparation for compounds of the present invention.

Example 1 describes the preparation of 1,1,3,5-tetramethyl-3-isopropylindan-6-ol formate ester, a compound of Formula [I] wherein $R_1$ is H, $R_2$ is OC(O)H, $R_3$ is $CH_3$, $R_4$ is $CH(CH_3)_2$, $R_5$ is $CH_3$, $R_6$ is H, $R_7$ is $CH_3$, and $R_8$ is $CH_3$.

Example 2 describes the preparation of 1,3,3,5-tetramethyl-1-isopropylindan-6-ol formate ester, a compound of Formula [I] wherein $R_1$ is H, $R_2$ is OC(O)H, $R_3$ is $CH_3$, $R_4$ is $CH_3$, $R_5$ is $CH_3$, $R_6$ is H, $R_7$ is $CH(CH_3)_2$, and $R_8$ is $CH_3$.

Examples 3 and 4 describe the preparation of 1-isopropyl-2,3,3,5-tetramethylindan-6-ol formate ester, a compound of Formula [I] wherein $R_1$ is H, $R_2$ is OC(O)H, $R_3$ is $CH_3$, $R_4$ is $CH_3$, $R_5$ is $CH_3$, $R_6$ is $CH_3$, $R_7$ is $CH(CH_3)_2$, and $R_8$ is H.

Example 5 describes the preparation of 1-isopropyl-2,3,3,4,6-pentamethylindan-5-ol formate ester, a compound of Formula [I] wherein $R_1$ is $CH_3$, $R_2$ is OC(O)H, $R_3$ is $CH_3$, $R_4$ is $CH(CH_3)_2$, $R_5$ is H, $R_6$ is $CH_3$, $R_7$ is $CH_3$, and $R_8$ is $CH_3$.

Example 6 describes the preparation of 1-isopropyl-2,3,3,6-tetramethylindan-5-ol formate ester, a compound of Formula [I] wherein $R_1$ is H, $R_2$ is OC(O)H, $R_3$ is $CH_3$, $R_4$ is $CH(CH_3)_2$, $R_5$ is H, $R_6$ is $CH_3$, $R_7$ is $CH_3$, and $R_8$ is $CH_3$.

Example 7 describes the preparation of 1-isopropyl-2,3,3,6-tetramethyl-4-methoxyindan-5-ol formate ester, a compound of Formula [I] wherein $R_1$ is $OCH_3$, $R_2$ is OC(O)H, $R_3$ is $CH_3$, $R_4$ is $CH(CH_3)_2$, $R_5$ is H, $R_6$ is $CH_3$, $R_7$ is $CH_3$, and $R_8$ is $CH_3$.

Example 8 describes the preparation of 1-isopropyl-2,3,3,4-tetramethyl-6-methoxyindan-5-ol formate ester, a compound of Formula [I] wherein $R_1$ is $CH_3$, $R_2$ is OC(O)H, $R_3$ is $OCH_3$, $R_4$ is $CH(CH_3)_2$, $R_5$ is H, $R_6$ is $CH_3$, $R_7$ is $CH_3$, and $R_8$ is $CH_3$.

Example 9 describes the preparation of 1,1,2,3,3,5-hexamethylindan-6-ol formate ester, a compound of Formula [I] wherein $R_1$ is H, $R_2$ is OC(O)H, $R_3$ is $CH_3$, $R_4$ is $CH_3$, $R_5$ is $CH_3$, $R_6$ is $CH_3$, $R_7$ is $CH_3$, and $R_8$ is $CH_3$.

Example 10 describes the preparation of 1,1,2,3,3,4-hexamethyl-6-methoxyindan 5-ol formate ester, a compound of Formula [I] wherein $R_1$ is $CH_3$, $R_2$ is OC(O)H, $R_3$ is $OCH_3$, $R_4$ is $CH_3$, $R_5$ is $CH_3$, $R_6$ is $CH_3$, $R_7$ is $CH_3$, and $R_8$ is $CH_3$.

Example 11 describes the preparation of 1,1,2,3,3,6-hexamethyl-4-methoxyindan-5-ol formate ester, a compound of Formula [I] wherein $R_1$ is $OCH_3$, $R_2$ is OC(O)H, $R_3$ is $CH_3$, $R_4$ is $CH_3$, $R_5$ is $CH_3$, $R_6$ is $CH_3$, $R_7$ is $CH_3$, and $R_8$ is $CH_3$.

These examples are intended to be illustrative only, and are not to be construed as limiting the scope of the appended claims.

EXAMPLE 1

Preparation of 1,1,3,5-Tetramethyl-3-Isopropylindan-6-ol Formate Ester

The starting material 1,1,3,4,4,6-hexamethyl-1,2,3,4-tetrahydronaphthalene (HMT) is prepared by substantially following the procedures of Frank, U.S. Pat. No. 4,877,911. Specifically, a 50 ml three-necked round bottom flask is charged with cyclohexane (9.55 g), anhydrous aluminum chloride (0.912 g), methyltrioctylammonium chloride (1.37 g) and stirred for about 5 minutes. To the flask is then added over a period of about 3 hours a mixture of neohexene (3.82 g), tertiary-butyl chloride (4.81g) and para-cymene (12.57 g). During the addition process, the temperature of the flask is maintained at about 20° C., with the aid of a temperature controller, automatic laboratory jack and dry ice/isopropanol bath. After addition is completed, the reaction is quenched with ice water (20 ml), and the resultant product washed with, in order, 5% aqueous hydrochloric acid, 10% aqueous sodium carbonate and water. All aqueous layers are then individually extracted with ether, the ether layers combined with the initial organic phase, and then evaporated to yield a product containing HMT. The HMT is further purified using standard fractional distillation techniques.

In accordance with Frank, U.S. Pat. No. 5,087,785, a 100 ml four necked round bottom flask is then charged with HMT (20 g) and dichloromethane (32.6 g), and cooled to 0° C. with a dry ice/isopropanol bath. To the flask is then added, with stirring, anhydrous aluminum chloride (2.507 g). The temperature of the flask is maintained between about 0° C. and 10° C., while the reaction is allowed to proceed for about 2.5 hours. The reaction is then quenched with ice water (25 ml), and the resultant product washed with deionized water. The aqueous layer is extracted twice with ether, the organics are combined, dried over potassium carbonate and rotoevaporated. The resultant product is a mixture of 1,1,3,5-tetramethyl 3-isopropylindane and 1,3,3,5-tetramethyl 1-isopropylindane. The compound 1,1,3,5-tetramethyl-3-isopropylindane is then separated using a vacuum spinning band fractional distillation apparatus.

Next, 1,1,3,5-tetramethyl-3-isopropylindane (12.96 g) is placed in a 1 liter three-necked round bottom flask equipped with a reflux condenser, a stirrer and a dropping funnel. In accordance with the general procedures described in *Organic Syntheses*, Collective Vol. 5, pp. 49–50, by A. Rieche, H. Gross, and E. Hoft, edited by H.E. Baumgarten, John Wiley and Sons (New York, N.Y. 1973), methylene chloride (37.5 ml) is added to the flask. The solution is then cooled in an ice bath, and titanium tetrachloride (19.0 g) is added over a period of about 3 minutes. While the solution is stirred and cooled, α,α-dichloromethyl methyl ether (5.75 g) is added dropwise over a 25 minute period. After the addition is complete, the mixture is stirred for about 5 minutes in the ice bath, for about 30 minutes without cooling, and for about 15 minutes at about 35° C. The reaction mixture is then poured into a separatory funnel containing about 50 g of crushed ice and is shaken thoroughly. The organic layer is separated, and the aqueous solution is extracted with two 10 ml portions of methylene chloride. The combined organic solution is washed three times with 10 ml portions of water. A crystal of hydroquinone is added to the methylene chloride solution, which is then dried over anhydrous sodium sulfate. After evaporation of the solvent, the residue is distilled to yield as a crude product, 6-formyl-1,1,3,5-tetramethyl-3-isopropylindane. The 6 formyl-1,1,3,5 tetramethyl-3-isopropylindane is then further purified using standard fractional distillation techniques.

The 6-formyl-1,1,3,5-tetramethyl-3-isopropylindane (7.32 g) is then treated with meta-chloroperbenzoic acid (16.3 g) (available from Aldrich Chemical Company, Milwaukee, Wis., in 60–65% purity) in methylene chloride (325 ml) at room temperature and rapidly stirred for between about 2 and 3 hours, using procedures similar to those described in Hannan et al., *J. Org. Chem.*, Vol. 44, pp. 2153–2158 (1979). To the resultant product is then added aqueous sodium thiosulfate (100 ml; 10% solution), and the solution stirred for 30 minutes. To the solution is then added additional aqueous sodium thiosulfate (250 ml) and the solution is vigorously shaken. The phases are separated, the aqueous phase extracted with methylene chloride (2×100 ml), and the organic phases washed successively with aqueous sodium thiosulfate (2×200 ml), and brine (200 ml). The organics are then dried over anhydrous sodium sulfate, combined, and subjected to rotoevaporation, resulting in 1,1,3,5 tetramethyl-3-isopropylindan-6-ol formate ester.

EXAMPLE 2

Preparation of
1,3,3,5-Tetramethyl-1-Isopropylindan-6-ol Formate Ester

HMT (20 g), prepared in accordance with Example 1, is reacted with dichloromethane in the presence of anhydrous aluminum chloride (2.507 g), also as described in Example 1. The resultant product is a mixture of 1,1,3,5-tetramethyl 3 isopropylindane and 1,3,3,5-tetramethyl 1 isopropylindane, which is separated using a vacuum spinning band distillation apparatus to isolate 1,3,3,5-tetramethyl-1-isopropylindane for further use.

The compound 1,3,3,5-tetramethyl-1-isopropylindane is then treated as described in Example 1 to yield the compound 6-formyl-1,3,3,5-tetramethyl-1-isopropylindane, which in turn is treated as in Example 1 to yield the compound 1,3,3,5-tetramethyl-1-isopropylindan-6-ol formate ester.

EXAMPLE 3

Preparation of
1-Isopropyl-2,3,3,5-Tetramethylindan-6-ol Formate Ester

To prepare 1-isopropyl-2,3,3,5-tetramethylindane, the procedures of Traas et al., U.S. Pat. No. 4,352,748 are substantially followed. Specifically, a solution of aluminum chloride (75 g) in nitromethane (50 ml) is added to a mixture of isobutyroyl chloride (49 g), nitromethane (50 ml) and toluene (100 ml), and stirred for one hour at about 10° C. The reaction mixture is poured over ice and extracted with ether. The ether solution is washed to neutrality, dried and evaporated. The residue is distilled under diminished pressure to obtain p-tolyl isopropyl ketone. The ketone (11 g) is then dissolved in methanol (50 ml), added to a solution of NaBH₄ (10 g) in a methanol/water mixture (100 ml; 1:1). The reaction mixture is stirred for one hour, and then poured into water and extracted with ether. The solution in ether is dried on anhydrous magnesium sulfate and evaporated to yield 2-methyl-1-(p-tolyl)propanol-1.

Next, thionyl chloride (20 ml) is added to 2-methyl-1-(p-tolyl)propanol-1 (10 g) and pyridine (2 ml), while maintaining the temperature between about 10° C. and 20° C. The reaction mixture is then stirred for half an hour, poured over ice, and extracted with ether. The solution in ether is washed neutral, dried and evaporated. The residue is distilled under diminished pressure to obtain 2-methyl-1-(p-tolyl)propyl chloride.

To the 2 methyl-1-(p-tolyl)propyl chloride (30 g) is added a solution of aluminum chloride (25 g) in nitromethane (100 ml), 2-methyl-2-butene (15 g) and nitromethane (50 ml), while maintaining the mixture at a temperature between about 5° C. and 10° C. After the reaction mixture is stirred for about 15 minutes, the mixture is poured over ice, and extracted with ether. The solution in ether is then washed to neutrality, dried and evaporated. The residue is distilled under diminished pressure to obtain 1-isopropyl-2,3,3,5-tetramethylindane.

The compound 1-isopropyl-2,3,3,5-tetramethylindane is then treated as described in Example 1 to yield 6-formyl-1-isopropyl-2,3,3,5-tetramethylindane, which in turn is treated as in Example 1 to yield 1-isopropyl-2,3,3,5-tetramethylindan-6-ol formate ester.

EXAMPLE 4

Preparation of
1-Isopropyl-2,3,3,5-Tetramethylindan-6-ol Formate Ester

To prepare the 1-isopropyl-2,3,3,5-tetramethylindane, the procedures of Traas et al., U.S. Pat. No. 4,352,748 are substantially followed. Specifically, methallyl chloride (24 g) is added to a mixture of toluene (92 g) and concentrated sulfuric acid (49 g), while maintaining the temperature at about 40° C. The reaction mixture is stirred for half an hour, after which time the layers are separated. The organic layer is washed neutral with soda solution, dried on magnesium sulfate and evaporated. The residue is distilled under diminished pressure to obtain 2-methyl-2 (para-tolyl)propyl chloride. A mixture of 2 methyl-2-(para-tolyl)propyl chloride (18 g) and tert-amyl chloride (10 g) is added to aluminum chloride (10 g) dissolved in nitromethane (50 ml), at a temperature of between about 5° C. and 10° C. The reaction mixture is allowed to warm to room temperature, with stirring, over a period of about one hour. The reaction mixture is then poured over ice, and extracted three times with ether. The solution in ether is washed to neutrality, dried on magnesium sulfate and evaporated. The residue is distilled under diminished pressure to yield 1-isopropyl-2,3,3,5-tetramethylindane.

The compound 1-isopropyl-2,3,3,5-tetramethylindane is then treated as described in Example 1 to yield 6-formyl 1-isopropyl-2,3,3,5-tetramethylindane, which in turn is treated as in Example 1 to yield 1-isopropyl-2,3,3,5-tetramethylindan-6-ol formate ester.

EXAMPLE 5

Preparation of
1-Isopropyl-2,3,3,4,6-Pentamethylindan-5-ol Formate Ester

Isopropylmagnesium chloride (2.0 M, 100 ml, 0.2 moles) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 3,5-dimethylbenzaldehyde (24.46 g) (which may be obtained from Lancaster Synthesis, Inc., Windham, N.H.). After about 2 hours, an aliquot of additional Grignard (20 ml) is added. The solution is then heated at 60° C. for about one hour, and quenched with aqueous NH₄Cl. The aqueous layer is then washed several times with methyl tert-butyl ether and rotoevaporated to yield a crude product mixture containing 2-methyl-1-[3',5'-dimethylphenyl]-1 propanol. The product mixture is then fractionated under reduced pressure to further purify the 2-methyl-1-[3',5'-dimethylphenyl-1-propanol compound.

Next, 2-methyl-1-[3',5'-dimethylphenyl-1-propanol is converted to 1-isopropyl 2,3,3,4,6-pentamethylindane by following procedures similar to those described in European Patent Application Publication No. 0 393 742. Specifically, to a stirred solution of 10 ml TiCl₄, in 120 ml dichloromethane which has been cooled to −5° C. under nitrogen, is added a mixture of 17.8 g 2-methyl-1-[3',5'-dimethylphenyl-1-propanol, and 14.0 g 2-methyl-2-butene over a two hour period. The reaction mixture is stirred for a further 30 min at −5° C. Thereafter, it is poured into a mixture of 200 ml water and 100 ml concentrated hydrochloric acid and stirred for 15 min. The organic phase is separated and the aqueous phase washed with brine with 50 ml dichloromethane. The combined organic phase is washed twice with 100 ml 10% hydrochloric acid solution, once with 100 ml water, twice with 100 ml 5% sodium carbonate solution, and finally, once again, with water. Solvent is then removed, yielding 1-isopropyl-2,3,3,4,6-pentamethylindane, which is further purified using reduced pressure fractional distillation techniques.

The compound 1-isopropyl-2,3,3,4,6-pentamethylindane is then treated as in Example 1 to yield 5-formyl-1-isopropyl-2,3,3,4,6-pentamethylindane, which in turn is treated as in Example 1 to yield 1-isopropyl-2,3,3,4,6-pentamethylindan-5-ol formate ester.

EXAMPLE 6

Preparation of 1-Isopropyl 2,3,3,6-Tetramethylindan-5-ol Formate Ester

Isopropylmagnesium chloride (2.0 M, 100 ml, 0.2 moles) (which may be obtained from Aldrich Chemical Company, Inc., Milwaukee, Wis.) in ether is added at room temperature to a 250 ml four necked round bottom flask equipped with an air stirrer, septum, Claisen adapter (thermocouple and dry ice condenser attached) and nitrogen inlet tube. To this is then slowly added meta tolualdehyde (24.46 g). After about 2 hours, an aliquot of Grignard (20 ml) is added. The reaction is then heated at 60° C. for about one hour, and quenched with aqueous NH₄Cl. The aqueous layer is then washed several times with methyl tert-butyl ether and rotoevaporated to yield a crude product mixture containing 2-methyl 1-[3'-methylphenyl]-1-propanol. The product mixture is then fractionated under reduced pressure further purify 2-methyl-1-[3'-methylphenyl]-1-propanol. The compound 2-methyl-1-[3'-methylphenyl]-1-propanol is then converted to 1-isopropyl-2,3,3,6-tetramethylindane by following the procedures of Example 5.

The compound 1-isopropyl 2,3,3,6-tetramethylindane is then treated as described in Example 5 to yield 5-formyl 1-isopropyl-2,3,3,6-tetramethylindane, which in turn is treated as in Example 1 to yield 1-isopropyl-2,3,3,6-tetramethylindan 5-ol formate ester.

EXAMPLE 7

Preparation of 1-Isopropyl 2,3,3,6-Tetramethyl-4-Methoxyindan-5-ol Formate Ester Isopropylmagnesium chloride (2.0 M, 100 ml, 0.2 moles) (which may be obtained from Aldrich Chemical Company, Inc., Milwaukee, Wis.) in ether is added at room temperature to a 250 ml four necked round bottom flask equipped with an air stirrer, septum, Claisen adapter (thermocouple and dry ice condenser attached) and nitrogen inlet tube. To this is then slowly added 3-methoxy-5-methyl benzaldehyde (24.46 g), which may be prepared in accordance with the procedures of Syper, *Tetrahedron Letters*, No. 37, pp. 4493–4498 (1966). After about 2 hours, an aliquot of Grignard (20 ml) is added. The solution is then heated at 60° C. for about one hour, and quenched with aqueous NH₄Cl. The aqueous layer is then washed several times with methyl tert-butyl ether and rotoevaporated to yield a crude product mixture containing 2 methyl-1-[3'-methoxy 5'-methylphenyl]-1-propanol. The product mixture is then fractionated under reduced pressure to further purify 2-methyl-1-[3'-methoxy-5'-methylphenyl]-1-propanol.

The compound 2-methyl-1-[3'-methoxy-5'-methylphenyl]-1-propanol is then converted to a mixture of 1-isopropyl-2,3,3,6-tetramethyl-4-methoxyindane and 1-isopropyl-2,3,3,4-tetramethyl-6-methoxyindane by following the procedures of Example 5. The mixture of indanes is then subjected to vacuum spinning band distillation techniques to separate out the 1-isopropyl 2,3,3,6-tetramethyl-4-methoxyindane compound.

The 1-isopropyl 2,3,3,6-tetramethyl-4-methoxyindane compound is then treated as described in Example 5 to yield 6-formyl-1-isopropyl-2,3,3,6-tetramethyl-4-methoxyindane, which in turn in treated as described in Example 1 to yield I-isopropyl-2,3,3,6-tetramethyl-4-methoxyindan-5 ol formate ester.

EXAMPLE 8

Preparation of 1-Isopropyl-2,3,3,4-Tetramethyl-6-Methoxyindan-5-ol Formate Ester The procedures of Example 7 are substantially carried out, except that the compound I-isopropyl-2,3,3,4-tetramethyl-6-methoxyindane is isolated from the indane mixture using vacuum spinning band distillation techniques for further use.

The compound 1-isopropyl-2,3,3,4-tetramethyl-6-methoxyindane is then treated as described in Example 5 to yield 6-formyl-1-isopropyl-2,3,3,4-tetramethyl 6-methoxyindane, which in turn is treated as in Example 1 to yield 1-isopropyl-2,3,3,4-tetramethyl-6-methoxyindan-5-ol formate ester.

EXAMPLE 9

Preparation of 1,I,2,3,3,5-Hexamethylindan-6-ol Formate Ester

A 100 ml four-necked round bottom flask equipped with an N₂ line, condenser, thermocouple-temperature controller, and addition funnel is charged with methylene chloride (9.79 g), and cooled to 15° C. with a dry ice/isopropanol bath. To the flask is then added, with stirring, anhydrous aluminum chloride (0.874 g). While maintaining a temperature of 15° C., a homogeneous mixture of para-cymene (21.7 g) and 2 methyl-2-butene (20.53 g, 0.2932 moles) is added to the flask over a period of about 30 minutes. The reaction is then allowed to proceed for about 2 additional hours at the same temperature. The flask contents are continuously stirred throughout the reaction.

The reaction is then quenched with cold deionized water (10 ml), and the resultant product further treated with 10% aqueous NaHCO3 and extracted with methylene chloride. After drying with anhydrous sodium sulfate, the organic solution was rotoevaporated to give a crude product containing 1,1,2,3,3,5-hexamethylindane, which is further purified using standard fractional distillation techniques.

The compound 1,1,2,3,3,5-hexamethylindane is then treated as described in Example 5 to yield 6-formyl-1,1,2,3,3,5-hexamethylindane, which in turn is treated as in Example 1 to yield 1,1,2,3,3,5-hexamethylindan-6-ol formate ester.

EXAMPLE 10

Preparation of 1,1,2,3,3,4-Hexamethyl-6-Methoxyindan-5-ol Formate Ester

Methylmagnesium bromide (3.0 M, 100 ml) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added a mixture of 2,3-dimethyl-4-methoxyacetophenone and 3,4-dimethyl-2-methoxyacetophenone (24.46 g). The mixture of acetophenones may be prepared using the Perrier modification (CH3C(O)Cl, aluminum chloride and methylene chloride) in accordance with the procedures of Perrier, *Chem. Ber.*, Vol. 33, pp. 819 et seq. (1900), and Perrier, *Bull. Soc. Chim.* France, pp. 859 et seq. (1904). After about 2 hours, an aliquot of additional Grignard (20 ml) is added. The solution is then heated at 60° C. for about one hour, and quenched with aqueous NH4Cl. The aqueous layer is then washed several times with methyl tert-butyl ether and rotoevaporated to yield a crude product mixture containing 1-methyl-1-[2'-methoxy-3',4'-dimethylphenyl]-ethanol or 1-methyl-1-[4'-methoxy-2',3'-dimethylphenyl]-ethanol. The product mixture is then subjected to spinning band distillation procedures to separate out the 1-methyl-1-[4'-methoxy-2',3'-dimethylphenyl]-ethanol compound. The compound 1-methyl-1-[4'-methoxy-2',3'-dimethylphenyl]-ethanol is then converted to 1,1,2,3,3,4-hexamethyl-6 methoxyindane by following the procedures of Example 5.

The 1,1,2,3,3,4-hexamethyl-6-methoxyindane (10.8 g) is then heated with copper(II) sulfate pentahydrate (18.04 g) and potassium peroxydisulfate (60.55 g) in acetonitrile and water (1:1, 500 ml) at reflux for about 15 to 20 minutes, following procedures similar to those described in Hauser et al., *Synthesis*, pp. 723–724 (1987). The mixture is then cooled to room temperature and methylene chloride (150 ml) is added. The layers are separated and the aqueous phase is further extracted with additional methylene chloride (2×70 ml). The combined organic solutions are dried with anhydrous sodium sulfate, filtered, and evaporated at reduced pressure to yield 5-formyl-1,1,2,3,3,4-hexamethyl-6-methoxyindane.

The 5-formyl-1,1,2,3,3,4-hexamethyl-6-methoxyindane compound is then treated as in Example 1 to yield 1,1,2,3,3,4-hexamethyl-6-methoxyindan-5-ol formate ester.

EXAMPLE 11

Preparation of 1,1,2,3,3,6-Hexamethyl-4-Methoxyindan 5-ol Formate Ester

The procedures of Example 10 are substantially carried out, except that the compound 1-methyl-1-[2'-methoxy 3',4'-dimethylphenyl]-ethanol is isolated from the indane mixture using standard fractional distillation techniques, and used to prepare 1,1,2,3,3,6-hexamethyl-4-methoxyindane.

The compound 1,1,2,3,3,6-hexamethyl-4-methoxyindane is then treated as described in Example 11 to yield 6-formyl 1,1,2,3,3,6-hexamethyl-4-methoxyindane, which in turn is treated as in Example 1 to yield 1,1,2,3,3,6-hexamethyl-4-methoxyindan-5-ol formate ester.

The disclosures of each patent and publication cited or described herein are hereby incorporated herein by reference, in their entirety.

Various modifications of the invention, in addition to those shown and described herein, will be readily apparent to those skilled in the art from the foregoing description. Such modifications are also intended to fall within the scope of the appended claims.

What is claimed is:

1. A compound of the formula:

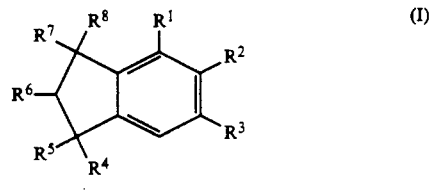

wherein
  $R^1$ is H, $CH_3$, $CH_2CH_3$, $OCH_3$ or OH,
  $R^2$ and $R^3$ are, independently, H, $CH_3$, $CH_2CH_3$, $OCH_3$, OH or OC(O)H,
  $R^4$ and $R^7$ are, independently, H, $CH_3$, $CH_2CH_3$ or $CH(CH_3)_2$,
  $R^5$ and $R^8$ are, independently H or $CH_3$, and
  $R^6$ is H, $CH_3$ or $CH_2CH_3$,
provided that
  (i) one of $R^2$ and $R^3$ is OC(O)H, and one of $R^2$ and $R^3$ is other than OC(O)H,
  (ii) when $R^1$ is H, then $R^2$ and $R^3$ are other than $OCH_3$ or OH,
  (iii) when $R^1$ is other than H, then $R^7$ is $CH_3$ or $CH_2CH_3$,
  (iv) no more than one of $R^4$, $R^6$ or $R^7$ is $CH_2CH_3$ or $CH(CH_3)_2$,
  (v) no more than one of $R^4$, $R^5$, $R^6$, $R^7$ and $R^8$ is H,
  (vi) when each of $R^1$, $R^3$, $R^4$ and $R^5$ are $CH_3$, then $R^8$ is H,
  (vii) when $R^4$ is $CH(CH_3)_2$, then at least one of $R^5$ or $R^6$ is H,
  (viii) when $R^7$ is $CH(CH_3)_2$, then at least one of $R^6$ or $R^8$ is H,
  (ix) when $R^1$ is $OCH_3$, then $R^2$ and $R^3$ are other than OH, and
  (x) when $R^1$ is OH, then $R^2$ and $R^3$ are other than OH or $OCH_3$.

2. A compound of claim 1 wherein $R^2$ is OC(O)H.

3. A compound of claim 1 wherein at least one of $R^1$, $R^2$ and $R^3$ are, independently, $OCH_3$ or OH.

4. A compound of claim 3 wherein at least one of $R^1$, $R^2$ and $R^3$ are $OCH_3$.

5. A compound of claim 1 wherein $R^1$ is H, $CH_3$, $CH_2CH_3$ or $OCH_3$, and $R^2$ and $R^3$ are, independently, H, $CH_3$, $CH_2CH_3$, $OCH_3$ or OC(O)H.

6. A compound of claim 5 wherein $R^1$ is H, $CH_3$ or $OCH_3$, and $R^2$ and $R^3$, independently, are H, $CH_3$, $OCH_3$ or OC(O)H.

7. A compound of claim 1 wherein at least one of $R^4$ or $R^7$ are H, $CH_3$ or $CH_2CH_3$.

8. A compound of claim 1 wherein $R^4$ and $R^7$ are, independently, $CH_3$, $CH_2CH_3$ or $CH(CH_3)_2$, and $R^5$ and $R^8$ are $CH_3$.

9. A compound of claim 8 wherein $R^6$ is $CH_3$ or $CH_2CH_3$.

10. A compound of claim 1 wherein $R^4$ is $CH(CH_3)_2$.

11. A compound of claim 1 wherein $R^1$ is $CH_3$, $R^2$ is OC(O)H, $R^3$ is $OCH_3$, $R^4$ is $CH_3$, $R^5$ is $CH_3$, $R^7$ is $CH_3$, $R^1$ is $CH_3$ and $R^8$ is $CH_3$.

12. A compound of claim 1 wherein $R^1$ is $OCH_3$, $R^2$ is OC(O)H, $R^3$ is $CH_3$, $R^4$ is $CH_3$, $R^5$ is $CH_3$, $R^6$ is $CH_3$, $R^7$ is $CH_3$ and $R^8$ is $CH_3$.

13. A compound of claim 1 wherein $R^1$ is $CH_3$, $R^2$ is OC(O)H, $R^3$ is $CH_3$, $R^4$ is $CH_2CH_3$, $R^5$ is $CH_3$, $R^6$ is H, $R^7$ is $CH_3$ and $R^8$ is $CH_3$.

14. A compound of claim 1 wherein $R^1$ is $CH_3$, $R^2$ is OC(O)H, $R^3$ is $OCH_3$, $R^4$ is $CH_2CH_3$, $R^5$ is $CH_3$, $R^6$ is H, $R^7$ is $CH_3$ and $R^8$ is $CH_3$.

15. A compound of claim 1 wherein $R^1$ is $CH_3$, $R^2$ is OC(O)H, $R^3$ is $OCH_3$, $R^4$ is $CH_3$, $R^5$ is $CH_3$, $R^6$ is H, $R^7$ is $CH_3$ and $R^8$ is $CH_3$.

16. A compound of claim 1 wherein $R^1$ is $OCH_3$, $R^2$ is OC(O)H, $R^3$ is $CH_3$, $R^4$ is $CH_2CH_3$, $R^5$ is $CH_3$, $R^6$ is H, $R^7$ is $CH_3$ and $R^8$ is $CH_3$.

17. A compound of claim 1 wherein $R^1$ is $OCH_3$, $R^2$ is OC(O)H, $R^3$ is $CH_3$, $R^4$ is $CH_3$, $R^5$ is $CH_3$, $R^6$ is H, $R^7$ is $CH_2CH_3$ and $R^8$ is $CH_3$.

18. A compound of claim 1 wherein $R^1$ is H, $R^2$ is OC(O)H, $R^3$ is $CH_3$, $R^4$ is $CH_3$, $R^5$ is $CH_3$, $R^6$ is $CH_3$, $R^7$ is $CH_3$ and $R^8$ is $CH_3$.

19. A compound of claim 1 wherein $R^1$ is H, $R^2$ is OC(O)H, $R^3$ is $CH_3$, $R^4$ is $CH_2CH_3$, $R^5$ is $CH_3$, $R^6$ is H, $R^7$ is $CH_3$ and $R^8$ is $CH_3$.

20. A compound of claim 1 wherein $R^1$ is H, $R^2$ is OC(O)H, $R^3$ is $CH_3$, $R^4$ is $CH_2CH_3$, $R^5$ is $CH_3$, $R^6$ is H, $R^7$ is $CH_2CH_3$ and $R^8$ is $CH_3$.

21. A compound of claim 1 wherein $R^1$ is H, $R^2$ is OC(O)H, $R^3$ is $CH_3$, $R^4$ is $CH(CH_3)_2$, $R^5$ is $CH_3$, $R^6$ is H, $R^7$ is $CH_3$ and $R^8$ is $CH_3$.

22. A compound of claim 1 wherein $R^1$ is H, $R^2$ is OC(O)H, $R^3$ is $CH_3$, $R^4$ is $CH_2CH_3$, $R^5$ is $CH_3$, $R^6$ is H, $R^7$ is $CH(CH_3)_2$ and $R^8$ is $CH_3$.

23. A compound of claim 1 wherein $R^1$ is $CH_3$, $R^2$ is OC(O)H, $R^3$ is $CH_3$, $R^4$ is $CH(CH_3)_2$, $R^5$ is H, $R^6$ is $CH_3$, $R^7$ is $CH_3$ and $R^8$ is $CH_3$.

24. A compound of claim 1 wherein $R^1$ is $CH_3$, $R^2$ is OC(O)H, $R^3$ is $OCH_3$, $R^4$ is $CH(CH_3)_2$, $R^5$ is H, $R^6$ is $CH_3$, $R^7$ is $CH_3$ and $R^8$ is $CH_3$.

25. A compound of claim 1 wherein $R^1$ is $OCH_3$, $R^2$ is OC(O)H, $R^3$ is $CH_3$, $R^4$ is $CH(CH_3)_2$, $R^5$ is H, $R^6$ is $CH_3$, $R^7$ is $CH_3$ and $R^8$ is $CH_3$.

26. A compound of claim 1 wherein $R^1$ is $OCH_3$, $R^2$ is OC(O)H, $R^3$ is $OCH_3$, $R^4$ is $CH(CH_3)_2$, $R^5$ is H, $R^6$ is $CH_3$, $R^7$ is $CH_3$ and $R^8$ is $CH_3$.

27. A compound of claim 1 wherein $R^1$ is H, $R^2$ is OC(O)H, $R^3$ is $CH_3$, $R^4$ is $CH(CH_3)_2$, $R^5$ is H, $R^6$ is $CH_3$, $R^7$ is $CH_3$ and $R^8$ is $CH_3$.

28. A compound of claim 1 wherein $R^1$ is H, $R^2$ is OC(O)H, $R^3$ is $CH_3$, $R^4$ is $CH_3$, $R^5$ is $CH_3$, $R^6$ is $CH_3$, $R^7$ is $CH(CH_3)_2$ and $R^8$ is H.

29. A fragrance composition comprising a compound of claim 1 in combination with at least one of a carrier and additional perfumery material.

30. A fragrance composition comprising a compound of claim 18 in combination with at least one of a carrier and additional perfumery material.

31. A fragrance composition comprising a compound of claim 19 in combination with at least one of a carrier and additional perfumery material.

32. A fragrance composition comprising a compound of claim 21 in combination with at least one of a carrier and additional perfumery material.

33. A fragrance composition comprising a compound of claim 22 in combination with at least one of a carrier and additional perfumery material.

34. A fragrance composition comprising a compound of claim 23 in combination with at least one of a carrier and additional perfumery material.

35. A fragrance composition comprising a compound of claim 28 in combination with at least one of a carrier and additional perfumery material.

36. A method of modifying the olfactory properties of a composition comprising adding thereto an olfactorily effective amount of a compound of claim 1.

37. A method of modifying the olfactory properties of a composition comprising adding thereto an olfactorily effective amount of a compound of claim 18.

38. A method of modifying the olfactory properties of a composition comprising adding thereto an olfactorily effective amount of a compound of claim 19.

39. A method of modifying the olfactory properties of a composition comprising adding thereto an olfactorily effective amount of a compound of claim 21.

40. A method of modifying the olfactory properties of a composition comprising adding thereto an olfactorily effective amount of a compound of claim 22.

41. A method of modifying the olfactory properties of a composition comprising adding thereto an olfactorily effective amount of a compound of claim 23.

42. A product produced by the method of claim 36.

* * * * *

UNITED STATES PATENT AND TRADEMARK OFFICE
CERTIFICATE OF CORRECTION

PATENT NO. : 5,292,720
DATED : March 8, 1994
INVENTOR(S) : Walter C. Frank It is certified that error appears in the above-identified patent and that said Letters Patent is hereby corrected as shown below:

Column 3, in the detailed description, line 65, change "$R^1$, $R^2$ and Rare" to -- $R^1$, $R^2$ and $R^3$ are --

Column 33, claim 15, lines 35-36, change "$R^7$ is $CH_3$" to -- $R^7$ is $CH_2CH_3$ --

Column 33, claim 20, line 51, change "$R^4$ is $CH_2CH_3$," to -- $R^4$ is $CH_3$ --

Column 33, claim 22, line 58, change "$R^4$ is $CH_2CH_3$," to -- $R^4$ is $CH_3$ --

Signed and Sealed this

Thirtieth Day of August, 1994

Attest:

BRUCE LEHMAN

*Attesting Officer*     *Commissioner of Patents and Trademarks*